(12) United States Patent
Gelfand et al.

(10) Patent No.: US 6,228,628 B1
(45) Date of Patent: May 8, 2001

(54) MUTANT CHIMERIC DNA POLYMERASE

(75) Inventors: David Harrow Gelfand; Fred Lawrence Reichert, both of Oakland, CA (US)

(73) Assignee: Roche Molecular Systems, Pleasanton, CA (US)

( * ) Notice: Subject to any disclaimer, the term of this patent is extended or adjusted under 35 U.S.C. 154(b) by 0 days.

(21) Appl. No.: 09/105,697

(22) Filed: Jun. 26, 1998

Related U.S. Application Data

(60) Provisional application No. 60/052,065, filed on Jul. 9, 1997.

(51) Int. Cl.⁷ .............................. C12N 9/12; C12N 1/20; C12N 1/16; C12N 15/00; C07H 21/04
(52) U.S. Cl. ................ 435/194; 435/252.3; 435/254.11; 435/320.1; 435/325; 536/23.2
(58) Field of Search ................ 435/194, 252.3, 435/254.11, 320.1, 325; 536/23.2

(56) References Cited

U.S. PATENT DOCUMENTS

| | | |
|---|---|---|
| 5,420,029 | 5/1995 | Gelfand et al. .................. 435/194 |
| 5,466,591 | 11/1995 | Abramson et al. .................. 435/194 |
| 5,474,920 | 12/1995 | Moses .................. 435/194 |
| 5,614,365 | 3/1997 | Tabor et al. .................. 435/6 |
| 5,948,614 * | 9/1999 | Chatterjee .................. 435/6 |

OTHER PUBLICATIONS

Derbyshire et al., Apr. 8, 1988, "Genetic and Crystallographic Studies of the 3',5'–Exonucleolytic Site of DNA Polymerase I," Science 240: 199–201.

Preprint of Bernad et al., 1989, "A Conserved 3'–5' Exonuclease Active site in Prokaryotic And Eukaryotic DNA Polymerases" Cell 59: 219–228.

Beese et al., 1991, "Structural basis for the 3'–5' exonuclease activity of *Escherichia coli* DNA polymerase I: a two metal ion mechanism," EMBO J. 10: 25–33.

Derbyshire et al., 1991, "The 3'–5' exonuclease of DNA polymerase I of *Escherichia coli*: contribution of each amino acid at the active site to the reaction," EMBO J. 10: 17–24.

Blanco et al., 1991, "A general structure for DNA–dependent DNA polymerases," Gene 100: 27–38.

Blanco et al., 1992, "Evidence favouring the hypothesis of a conserved 3'–5' exonuclease active site in DNA–dependent DNA polymerases," Gene 112: 139–144.

Soengas et al., 1992, "Site directed mutagenesis at the EXO III motif of ø29 DNA polymerase; overlapping structural domains for the 3'–5' exonuclease and strand–displacement activities DNA," EMBO J. 11:4227–37.

Gutman et al., 1993, "Conserved sites in the 5'–3' exonuclease domain of *Escherichia coli* DNA polymerase," Nucleic Acids Research, 21: 4406–4407.

Parker et al., Oct. 1996, "AmpliTaq® DNA Polymerase, FS Dye–Terminator Sequencing: Analysis of Peak Height Patterns," BioTechniques 21: 694–699.

Xu et al., 1997, "Biochemical and Mutational Studies of the 5'–3' Exonuclease of DNA Polymerase of *Escherichia coli*," J. Mol. Biol. 268: 284–302.

* cited by examiner

*Primary Examiner*—Ponnathapu Achutamurthy
*Assistant Examiner*—Richard Hutson
(74) *Attorney, Agent, or Firm*—Douglas A. Petry

(57) ABSTRACT

Mutant, chimeric thermostable DNA polymerases are provided, along with purified DNA sequences that encode the enzymes. Also provided are methods for producing and using the enzymes.

63 Claims, 8 Drawing Sheets

FIGURE 1A

```
Tma      =  Thermatoga maritima     (SEQ ID NO: 1)
Taq      =  Thermus aquaticus       (SEQ ID NO: 2)
Tfl      =  Thermus flavis          (SEQ ID NO: 3)
Tth      =  Thermus thermophilis    (SEQ ID NO: 4)
TZ05     =  Thermus species Z05     (SEQ ID NO: 5)
Tca      =  Thermus caldofilus      (SEQ ID NO: 6)
Tsps17   =  Thermus species sps17   (SEQ ID NO: 7)
Tfi      =  Thermus filiformus      (SEQ ID NO: 8)
```

```
                            *                                                  *
Tma      .........MARLFLFDGTALAYRAYYALDRSLSTSTGIPTNATYGVARMLVRFIKDHI              50
Taq      MRGMLPLFEPKGRVLLVDGHHLAYRTFHAL.KGLTTSRGEPVQAVYGFAKSLLKALKE...             57
Tfl      .MAMLPLFEPKGRVLLVDGHHLAYRTFFAL.KGLTTSRGEPVQAVYGFAKSLLKALKE...             56
Tth      MEAMLPLFEPKGRVLLVDGHHLAYRTFFAL.KGLTTSRGEPVQAVYGFAKSLLKALKE...             57
TZ05     MKAMLPLFEPKGRVLLVDGHHLAYRTFFAL.KGLTTSRGEPVQAVYGFAKSLLKALKE...             57
Tca      MEAMLPLFEPKGRVLLVDGHHLAYRTFFAL.KGLTTSRGEPVQAVYGFAKSLLKALKE...             57
Tsps17   ...MLPLFEPKGRVLLVDGHHLAYRTFFAL.KGLTTSRGEPVQAVYGFAKSLLKALKE...             54
Tfi      ...MLPLLEPKGRVLLVDGHHLAYRTFFAL.KGLTTSRGEPVQAVYGFAKSLLKALKE...             54

*    * **        *                                          *
Tma      IVGK.DYVAVAFDKKAATFRHKLLETYKAQRPKTPDLLIQQLPYIKKLVEALGMKVLVEVEG            110
Taq      ..DG.DAVIVVFDAKAPSFRHEAYGGYKAGRAPTPEDFPRQLALIKELVDLLGLARLEVPG            115
Tfl      ..DG.DVVVVVFDAKAPSFRHEAYEAYKAGRAPTPEDFPRQLALIKELVDLLGIVRLEVPG            114
Tth      ..DGYKAVFVVFDAKAPSFRHEAYEAYKAGRAPTPEDFPRQLALIKELVDLLGFTRLEVPG            116
TZ05     ..DGYKAVFVVFDAKAPSFRHEAYEAYKAGRAPTPEDFPRQLALIKELVDLLGFTRLEVPG            116
Tca      ..DGYKAVFVVFDAKAPSFRHEAYEAYKAGRAPTPEDFPRQLALIKELVDLLGFTRLEVPG            116
Tsps17   ..DGEVAI.VVFDAKAPSFRHEAYEAYKAGRAPTPEDFPRQLALIKELVDLLGIVRLEVPG            112
Tfi      ..DGEVAI.VVFDAKAPSFRHEAYEAYKAGRAPTPEDFPRQLALIKELVDLLGIVRLEVPG            112
```

FIGURE 1B

```
                    *  **      *                                                  *  *
Tma     YEADDIIATLAVKGLPLFDEIFIVTGDKDMLQIVNEKIKVWRIVKGISDLELYDAQKVKE              170
Taq     YEADDVLASLAKKAEKEGYEVRILTADKDLYQLLSDRIHVLH.....PEGYLITPAWLWE              170
Tfl     FEADDVLATLAKRAEKEGYEVRILTADRDLYQLLSERIAILH.....PEGYLITPAWLYE              169
Tth     YEADDVLATLAKKAEKEGYEVRILTADRDLYQLVSDRVAVLH.....PEGHLITPEWLWE              171
TZ05    FEADDVLATLAKKAEKEGYEVRILTADRDLYQLVSDRVAVLH.....PEGHLITPEWLWE              171
Tca     YEADDVLATLAKNPEKEGYEVRILTADRDLDQLVSDRVAVLH.....PEGHLITPEWLWQ              171
Tsps17  FEADDVLATLAKKAEREGYEVRILSADRDLYQLLSDRIHLLH.....PEGEVLTPGWLQE              167
Tfi     FEADDVLATLARKAEREGYEVRILSADRDLYQLLSDRIHLLH.....PEGEVLTPGWLQE              167

*           *    *
Tma     KYGVEPQQIPDLLALTGDEIDNIPGVTGIGEKTAVQLLEKYKDLEDILNHVRELPQ.KVRK              230
Taq     KYGLRPDQWADYRALTGDESDNLPGVKGIGEKTARKLLEEWGSLEALLKNLDRLKP.AIRE              230
Tfl     KYGLRPEQWVDYRALAGDPSDNLPGVKGIGEKTAQRLIREWGSLENLFQHLDQVKP.SLRE              229
Tth     KYGLRPEQWVDFRALVGDPSDNLPGVKGIGEKTALKLLKENLLKENLDRVKPENVRE              232
TZ05    KYGLKPEQWVDFRALVGDPSDNLPGVKGIGEKTALKLLKEWGSLENLIKNLDRVKPESVRE              232
Tca     KYGLKPEQWVDFRALVGDPSDNLPGVKGIGEKTALKLLKEWGSLENLLKNLDRVKPENVRE              232
Tsps17  RYGLSPERWVEYRALVGDPSDNLPGVPGIGEKTALKLLKEWGSLEAILKNLDQVKPERVRE              228
Tfi     RYGLSPERWVEYRALVGDPSDNLPGVPGIGEKTALKLLKEWGSLEAILKNLDQVKPERVWE              228

Tma     ALLRDRENAILSKKLAILETNVPIEINWEELRYQGYDREKLLPLLKELEFASIMKELQLYE              291
Taq     KILAHMDDLKLSWDLAKVRTDLPLEVDFGRRREP..DRERLRAFLERLEFGSLLHEFGLLE              289
Tfl     KLQAGMEALALSRKLSQVHTDLPLEVDFGRRRTP..NLEGLRAFLERLEFGSLLHEFGLLE              288
Tth     KIKAHLEDLRLSLELSLELSRVRTDLPLEVDFGRREP..DREGLRAFLERLEFGSLLHEFGLLE            291
TZ05    RIKAHLEDLRLSLELSRVRSDLPLEVDFARRREP..DREGLRAFLERLEFGSLLHEFGLLE              291
Tca     KIKAHLEDLRLSLELSRVRTDLPLEVDLAQGREP..DREGLRAFLERLEFGSLLHEFGLLE              291
Tsps17  AIRNNLDKLQMSLELSRLRTDLPLEVDFAKRREP..DWEGLKAFLERLEFGSLLHEFGLLE              287
Tfi     AIRNNLDKLQMSLELSRLRTDLPLEVDFAKRREP..DWEGLKAFLERLEFGSLLHEFGLLE              287
```

MUTANT CHIMERIC DNA POLYMERASE

This application claims priority to U.S. Provisional Application Ser. No. 60/052,065, filed Jul. 9, 1997, which is incorporated herein by reference.

BACKGROUND OF THE INVENTION

1. Field of the Invention

The present invention relates to a mutant chimeric thermostable DNA polymerase, methods for its synthesis, and methods for its use. The enzyme is useful in many recombinant DNA techniques, especially nucleic acid sequencing and nucleic acid amplification by the polymerase chain reaction (PCR).

2. Background Art

Thermostable DNA polymerases, which catalyze the template-directed polymerization of deoxyribonucleoside triphosphates (dNTPs) to form DNA, are used in a variety of in vitro DNA synthesis applications, such as DNA sequencing and DNA amplification. Typically, naturally occurring DNA polymerases strongly discriminate against the incorporation of nucleotide analogues. This property contributes to the fidelity of DNA replication and repair. However, the incorporation of nucleotide analogues is useful for many DNA synthesis applications, in particular, in DNA sequencing.

DNA sequencing reactions using the chain termination method initially described by Sanger et al., 1977, *Proc. Natl. Acad. Sci.* 74:5463–5467, incorporated herein by reference, rely on an unconventional substrate, dideoxynucleoside triphosphate (ddNTP), for termination of synthesis. In the chain termination method, both the DNA polymerase's conventional substrate (dNTP) and a chain-terminating, unconventional substrate (ddNTP or labeled ddNTP) are present in the reaction. Synthesis proceeds until a ddNTP is incorporated. To insure that the chain-terminating ddNTPs are incorporated at a suitable rate, the inherent discrimination of the previously utilized DNA polymerases against the incorporation of ddNTPs was overcome by providing an excess of ddNTP.

Dye-terminator sequencing, a variant of the chain termination method, uses ddNTPs labeled with fluorescent dyes, such as fluorescein or rhodamine, to terminate synthesis and, simultaneously, to label the synthesized DNA. The presence of a dye label on the ddNTP can exacerbate the discrimination by the DNA polymerase against the incorporation of the unconventional substrate.

Typically, sequencing by the chain termination method is carried out using repeated steps of primer extension followed by heat denaturation of the primer extension product-template duplex. This embodiment, referred to as cycle sequencing, is carried out in a thermal cycler using a thermostable DNA polymerase. Kits for carrying out cycle sequencing are commercially available from, for example, Perkin Elmer, Norwalk, Conn.

Thermostable DNA polymerases derived from a variety of organisms have been described extensively in the literature and are well known to one of skill in the art. Particular examples include DNA polymerases from a variety of species of the genus Thermus (see U.S. Pat. No. 5,466,591), in particular from *Thermus aquaticus* (Taq DNA polymerase) described in U.S. Pat. Nos. 4,889,818; 5,352,600; and 5,079,352; and the DNA polymerase from *Thermatoga maritima* (Tma DNA polymerase) described in U.S. Pat. Nos. 5,374,553 and 5,420,029; all of which are incorporated herein by reference.

DNA polymerases typically possess one or more associated exonucleolytic activities. For example Tma DNA polymerase catalyzes the exonucleolytic removal of nucleotides from the 5'-end of a double-stranded DNA (referred to as 5' to 3' exonuclease activity or 5'-nuclease activity) as well as from the 3'-end of a single- or double-stranded DNA (referred to as 3' to 5' exonuclease activity). In contrast, DNA polymerases from the genus Thermus possess only 5'-nuclease activity. A review of thermostable DNA polymerases and their associated activities is found in Abramson, 1995, in PCR Strategies, (Innis et al. ed., Academic Press, Inc.). For use in DNA sequencing, a DNA polymerase that lacks associated exonucleolytic activity, either 5'-nuclease activity or 3' to 5' exonuclease activity, is preferred. Mutant forms of a number of thermostable DNA polymerases which lack 5'-nuclease activity are described in U.S. Pat. No. 5,466,591, incorporated herein by reference.

European Patent Application 0 655 506, incorporated herein by reference, describes a mutated DNA polymerase with an enhanced ability to incorporate dideoxynucleotides (see also U.S. Pat. No. 5,614,365, incorporated herein by reference). The mutation is a point mutation corresponding to amino acid 526 of T7 DNA polymerase. Examples of such mutations include mutations in amino acid 667 of Taq DNA polymerase.

AmpliTaq® DNA polymerase, FS, a mutant form of Taq DNA polymerase that has essentially no 5'-nuclease activity and incorporates an F667Y mutation, is sold as a component of DNA cycle sequencing kits by Perkin Elmer, Norwalk, Conn. The F667Y mutation results in a significant reduction in the discrimination against ddNTPs. This property greatly improves the sequencing data obtained from a dye-terminator sequencing reaction and reduces the amount of ddNTPs required for each sequencing reaction. However, the use of AmpliTaq® DNA polymerase, FS has not eliminated problems with non-uniformity of peak heights in the sequencing trace when used with the standard rhodamine dye family-labeled ddNTPs. An analysis of the peak height patterns obtained using AmpliTaq® DNA polymerase, FS in dye-terminator cycle sequencing reactions is described in Parker et al., 1996, BioTechniques 21(4):694–699, incorporated herein by reference.

Conventional techniques of molecular biology and nucleic acid chemistry, which are within the skill of the art, are explained fully in the literature. See, for example, Sambrook et al., 1989, *Molecular Cloning—A Laboratory Manual*, Cold Spring Harbor Laboratory, Cold Spring Harbor, N.Y.; *Oligonucleotide Synthesis* (M. J. Gait, ed., 1984); *Nucleic Acid Hybridization* (B. D. Hames and S. J. Higgins. eds., 1984); and a series, *Methods in Enzymology* (Academic Press, Inc.), all of which are incorporated herein by reference. All patents, patent applications, and publications cited herein, both supra and infra, are incorporated herein by reference.

SUMMARY OF THE INVENTION

The present invention relates to mutant, chimeric thermostable DNA polymerases that possess significantly improved properties relative to previously described thermostable DNA polymerases. The DNA polymerase yields substantial improvements when used in DNA sequencing reactions. In particular, the DNA polymerase of the invention provides the following combination of advantageous properties:

1. improved incorporation of ddNTPs;
2. improved uniformity of peak heights in DNA sequencing traces, in particular when used with dye-labeled ddNTPs in a cycle sequencing reaction;

3. reduced rate of pyrophosphorolysis of dye-labeled ddNTPs; and 4. improved incorporation of dITP.

Furthermore, the DNA polymerase can be easily and efficiently expressed to a high level in a recombinant expression system, thereby facilitating commercial production of the enzyme. The combination of properties possessed by the DNA polymerase of the present invention represent a significant advantage over thermostable DNA polymerases previously described in the literature.

The chimeric DNA polymerases of the present invention consist of an N-terminal region derived from the 5'-nuclease domain of a Thermus species DNA polymerase and a C-terminal region derived from the 3' to 5' exonuclease and polymerase domains of Tma DNA polymerase. The N-terminal region contains at least a region of the Thermus species DNA polymerase corresponding to amino acids 1–138 of Tma DNA polymerase and may contain up to the entire 5'-nuclease domain of the Thermus species DNA polymerase. The C-terminal region contains, in addition to the 3' to 5' exonuclease and polymerase domains of Tma DNA polymerase, a portion of the 5'-nuclease domain of Tma DNA polymerase corresponding to the portion of the 5'-nuclease domain of the Thermus species DNA polymerase not present in the N-terminal region.

Thus, the chimeric DNA polymerase of the present invention consists of an N-terminal region and a C-terminal region, wherein said N-terminal region consists of amino acids 1 through n of a Thermus species DNA polymerase, wherein n is an amino acid position within a region of the Thermus species DNA polymerase corresponding to amino acids 138–291 of Tma DNA polymerase, and wherein said C-terminal region consists of amino acids m+1 through 893 of Tma DNA polymerase, wherein amino acid m in Tma DNA polymerase corresponds to amino acid n in the Thermus species DNA polymerase when Tma DNA polymerase and the Thermus species DNA polymerase are aligned as in the figures.

The chimeric DNA polymerase of the present invention is modified by a F730Y mutation in the DNA polymerase domain derived from Tma DNA polymerase, which increases the ability of the DNA polymerase to incorporate dideoxynucleotides.

In one embodiment, the 5'-nuclease domain of the chimeric DNA polymerase contains at least one point mutation that substantially reduces or, preferably, inactivates the 5'-nuclease activity. The mutation can be present either in the N-terminal, which is derived from the 5'-nuclease domain of the Thermus species DNA polymerase, or the portion of the C-terminal region that is derived from 5'-nuclease domain of Tma DNA polymerase, if present. Suitable mutations are those point mutations (single amino acid substitution or deletion mutations) that substantially reduce or, preferably, inactivate the 5'-nuclease activity in the source DNA polymerase. Thus, either the N-terminal region is modified by at least one amino acid substitution or deletion that substantially reduces or eliminates 5'-nuclease activity in the Thermus species DNA polymerase, or said C-terminal region is modified by at least one amino acid substitution or deletion within the region that is amino acids m+1 to 291 of Tma DNA polymerase that substantially reduces or eliminates 5'-nuclease activity in Tma DNA polymerase.

Amino acid positions which are critical to the 5'-nuclease activity of a DNA polymerase are well known, as described herein. A substitution of an amino acid at one or more of these critical positions or a deletion of an amino acid at one or more of these critical positions typically results in a decrease in the 5'-nuclease activity. Preferably, the chimeric DNA polymerase contains a mutation that substantially reduces or inactivates the 5'-nuclease activity.

In one embodiment, the C-terminal region, which contains the 3' to 5' exonuclease domain derived from Tma DNA polymerase, contains at least one point mutation that substantially reduces or, preferably, inactivates the 3' to 5' exonuclease activity in Tma DNA polymerase.

Amino acid positions which are critical to the 3' to 5' exonuclease activity of a DNA polymerase are well known, as described herein. A substitution of an amino acid at one or more of these critical positions or a deletion of an amino acid at one or more of these critical positions typically results in a decrease in the 3' to 5' nuclease activity. In a preferred embodiment, the C-terminal region contains a D323A and a E325A mutation, which inactivate the 3' to 5' exonuclease activity.

In one embodiment, the N-terminal region is derived from Taq DNA polymerase. In a preferred embodiment, the N-terminal region consists of amino acids 1–190 of Taq DNA polymerase, and the C-terminal region consists of amino acids 191–893 of Tma DNA polymerase. In a particular preferred embodiment, designated F730YTma30 DNA Polymerase, the N-terminal region consists of amino acids 1–190 of Taq DNA polymerase and contains a G46D mutation, and the C-terminal region consists of amino acids 191–893 of Tma DNA polymerase and contains D323A, E325A, and F730Y mutations.

Another aspect of the present invention relates to the purified DNA (chimeric gene) which encodes the mutant, chimeric thermostable DNA polymerase of the invention, recombinant DNA vectors which contain the DNA, and host cells transformed with the recombinant DNA vectors. DNA sequences which differ only by silent nucleotide changes (i.e., which encode the same amino acid sequence) are within the intended scope of the invention.

In a preferred embodiment of the invention, the purified DNA consists of nucleotides 1–570 of a gene encoding Taq DNA polymerase modified to encode the G46D mutation, and nucleotides 571–2679 of a gene encoding Tma DNA polymerase modified to encode the D323A, E325A, and F730Y mutations.

Another aspect of the invention relates to methods for preparing the mutant, chimeric thermostable DNA polymerase of the invention using the purified DNA of the present invention. A recombinant expression vector is expressed in a host cell, and the expressed protein is purified from the host cell.

BRIEF DESCRIPTION OF THE DRAWINGS

FIGS. 1A and 1B provide an amino acid sequence alignment of the 5'-nuclease domains of Tma DNA polymerase and DNA polyermases from seven species of the genus Thermus. Amino acids which are critical to the 5'-nuclease activity are indicated by asterisks.

DETAILED DESCRIPTION OF THE INVENTION

Figure 2A:
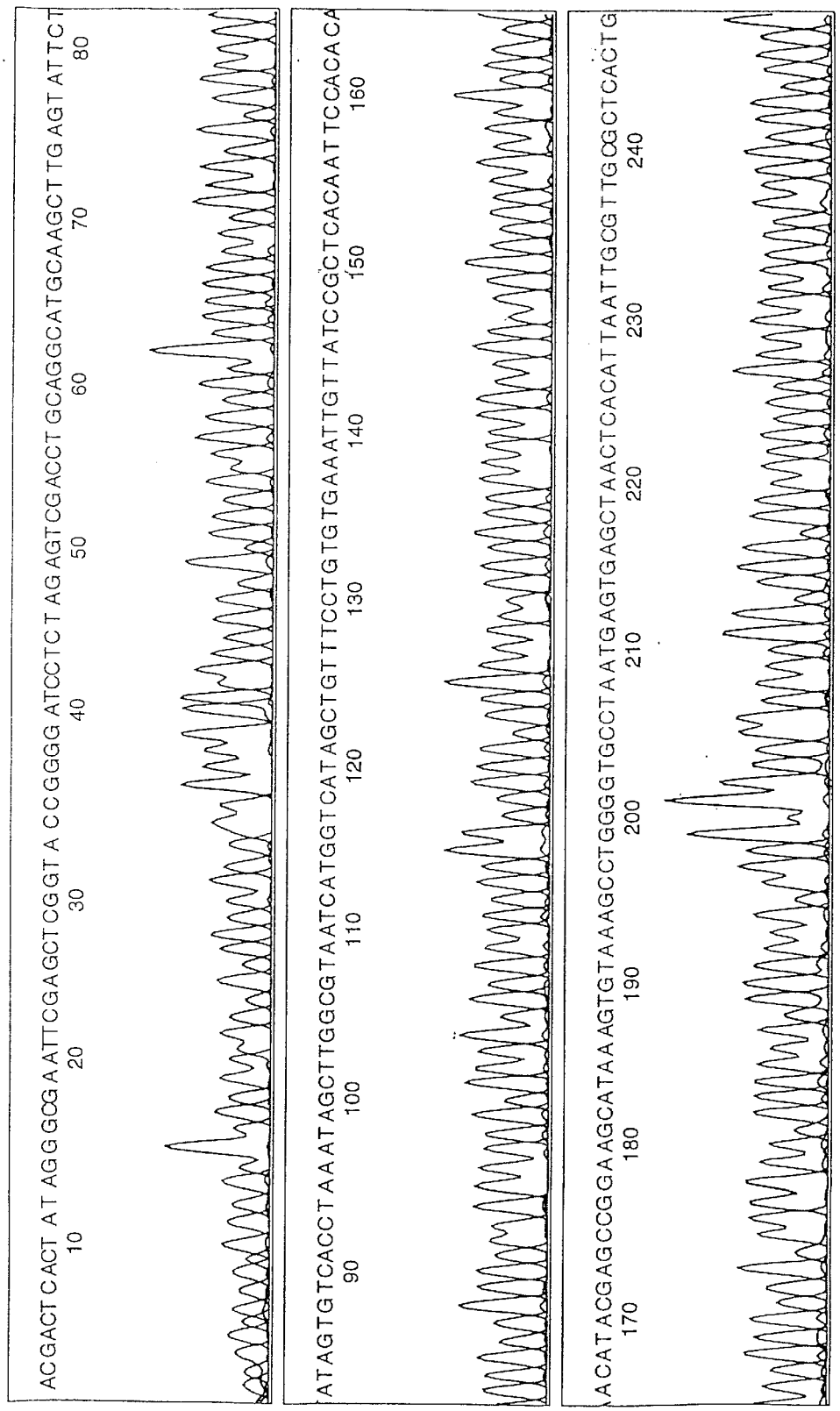
FIGS. 2A, 2B, and 2C provide a sequencing trace from the cycle sequencing reaction using F730YTma30 DNA Polymerase described in Example 5.

The present invention provides a mutant chimeric thermostable DNA polymerase and means for producing the enzyme. To facilitate understanding of the invention, a number of terms are defined below.

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, positive retroregulatory elements (see U.S. Pat. No. 4,666,848, incorporated herein by reference), and possibly other sequences. Eucaryotic cells are known to utilize promoters, polyadenylation signals, and enhancers.

The term "expression clone" refers to DNA sequences containing a desired coding sequence and control sequences in operable linkage, so that hosts transformed with these sequences are capable of producing the encoded proteins. The term "expression system" refers to a host transformed with an expression clone. To effect transformation, the expression clone may be included on a vector; however, the relevant DNA may also be integrated into the host chromosome.

The term "gene" refers to a DNA sequence that comprises control and coding sequences necessary for the production of a recoverable bioactive polypeptide or precursor.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "oligonucleotide" as used herein is defined as a molecule comprised of two or more deoxyribonucleotides or ribonucleotides. The exact size will depend on many factors, which in turn depends on the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference.

The term "primer" as used herein refers to an oligonucleotide which is capable of acting as a point of initiation of synthesis when placed under conditions in which primer extension is initiated. Synthesis of a primer extension product which is complementary to a nucleic acid strand is initiated in the presence of the requisite four different nucleoside triphosphates and a thermostable DNA polymerase in an appropriate buffer at a suitable temperature. A "buffer" includes cofactors (such as divalent metal ions) and salt (to provide the appropriate ionic strength), adjusted to the desired pH.

A primer that hybridizes to the non-coding strand of a gene sequence (equivalently, is a subsequence of the coding strand) is referred to herein as an "upstream" primer. A primer that hybridizes to the coding strand of a gene sequence is referred to herein as an "downstream" primer.

The terms "restriction endonucleases" and "restriction enzymes" refer to enzymes, typically bacterial in origin, which cut double-stranded DNA at or near a specific nucleotide sequence.

The term "thermostable enzyme", as used herein, refers to an enzyme which is stable to heat and has an elevated temperature reaction optimum. The thermostable enzyme of the present invention catalyzes primer extension optimally at a temperature between 60 and 90° C., and is usable under the temperature cycling conditions typically used in cycle sequence reactions and polymerase chain reaction amplifications (described in U.S. Pat. No. 4,965,188, incorporated herein by reference).

As used herein, a "point mutation" in an amino acid sequence refers to either a single amino acid substitution or single amino acid deletion. A point mutation preferably is introduced into an amino acid sequence by a suitable codon change in the encoding DNA.

Individual amino acids in a sequence are represented herein as AN, wherein A is the standard one letter symbol for the amino acid in the sequence, and N is the position in the sequence. Mutations within an amino acid sequence are represented herein as $A_1NA_2$, wherein $A_1$ is the standard one letter symbol for the amino acid in the unmutated protein sequence, $A_2$ is the standard one letter symbol for the amino acid in the mutated protein sequence, and N is the position in the amino acid sequence. For example, a G46D mutation represents a change from glycine to aspartic acid at amino acid position 46. The amino acid positions are numbered based on the full-length sequence of the protein from which the region encompassing the mutation is derived. Thus, in the present invention, mutations in the region of the protein which are derived from a Thermus species DNA polymerase are numbered according to the full-length Thermus species DNA polymerase sequence, whereas mutations in the region derived from Tma DNA polymerase are numbered according to the full-length Tma DNA polymerase sequence. Representations of nucleotides and point mutations in DNA sequences are analogous.

As used herein, a "chimeric" protein refers to a protein whose amino acid sequence represents a fusion product of subsequences of the amino acid sequences from at least two distinct proteins. A chimeric protein preferably is not produced by direct manipulation of amino acid sequences, but, rather, is expressed from a "chimeric" gene that encodes the chimeric amino acid sequence. The chimeric proteins of the present invention consist of an amino-terminal (N-terminal) region derived from a Thermus species DNA polymerase and a carboxy-terminal (C-terminal) region derived from Tma DNA polymerase. The N-terminal region refers to a region extending from the N-terminus (amino acid position 1) to an internal amino acid. Similarly, the C-terminal region refers to a region extending from an internal amino acid to the C-terminus. In the chimeric proteins of the present invention, the N-terminal region extends from the N-terminus (amino acid position 1) to the beginning of the C-terminal region, which extends to the C-terminus. Thus, taken together, the N-terminal and C-terminal regions encompass the entire amino acid sequence.

The exonucleolytic activities associated with DNA polymerases (3' to 5' exonuclease activity and 5'-nuclease activity, also referred to as 5' to 3' exonuclease activity) and methods of measuring these activities are well known in the art. As used herein, an activity is "substantially reduced" if reduced to less than about 20%, preferably to less than about 10%, and more preferably to less than about 1%, of the activity present in the unmutated enzyme. An activity is "inactivated" or "essentially inactivated" if reduced to a level which is negligible for the purpose of the enzyme's typical or preferred use.

The Thermostable DNA Polymerase of the Invention

The thermostable DNA polymerase of the present invention is a chimeric DNA polymerase in which the N-terminal region consists of an N-terminal region of a Thermus species DNA polymerase and the C-terminal region consists of a C-terminal region of Tma DNA polymerase. The N-terminal region from the Thermus species DNA polymerase encompasses a portion of, or all of, the 5'-nuclease domain. The C-terminal region from Tma DNA polymerase encompasses a portion, or possibly none, of the 5'-nuclease domain and the entire 3' to 5' exonuclease and DNA polymerase domains. The portion of the 5'-nuclease domain of Tma DNA polymerase encompassed by the C-terminal region of the chimeric protein will correspond to that portion of the 5'-nuclease domain of the Thermus species DNA polymerase not encompassed by the N-terminal region of the chimeric protein.

The chimeric DNA polymerase additionally contains the F730Y mutation, which increases the efficiency with which the DNA polymerase incorporates ddNTPs. The chimeric DNA polymerase preferably also contains one or more point mutations which significantly reduce or eliminate the 5'-nuclease activity and one or more point mutations which significantly reduce or eliminate the 3' to 5' exonuclease activity.

1. The Chimeric Protein Domains

DNA polymerases from species of the genus Thermus and Tma DNA polymerase are similar in overall structure. In these DNA polymerases, the exonuclease and DNA polymerase activities of the enzymes are present in discrete regions of the protein (the activity domains). The approximate activity domains of a representative Thermus species DNA polymerase, Taq DNA polymerase, and Tma DNA polymerase are shown in the table below (see also U.S. Pat. No. 5,420,029). The homologous activity domains which encode 5'-nuclease activity, and those which encode DNA polymerase activity, are approximately the same length (see FIGS. 1A and 1B). The difference in length between the region that encodes 3' to 5' exonuclease activity in Tma DNA polymerase and the corresponding region in Taq DNA polymerase corresponds to the lack of 3' to 5' exonuclease activity in Taq DNA polymerase.

| | Activity Domains (approximate amino acid positions) | | |
|---|---|---|---|
| | 5'-nuclease | 3' to 5' exonuclease | Polymerase |
| Taq DNA polymerase | 1–289 | — | 423–832 |
| Tma DNA polymerase | 1–291 | 292–484 | 485–893 |

Significant amino acid sequence similarity exists between Thermus species DNA polymerases and Tma DNA polymerase. For example, an amino acid sequence comparison of a representative Thermus species DNA polymerase, Taq DNA polymerase, and Tma DNA polymerase using the GAP computer program (Genetics Computer Group, Madison, Wis.) with the default parameter values, indicates that the amino acid sequences are approximately 44% identical and 66% similar over either the entire amino acid sequences or over the 5'-nuclease domains.

Because of the overall structural and sequence similarity, the chimeric enzyme preserves the overall structure and activity domains present in Tma DNA polymerase. The essential change is that the amino acid sequence of the N-terminal region of the chimeric enzyme is that of the corresponding region of a Thermus species DNA polymerase. Thus, the chimeric enzyme of the present invention corresponds to a mutated Tma DNA polymerase, wherein the 5'-nuclease domain has been replaced by the corresponding domain from a Thermus species DNA polymerase. The "corresponding domain" is defined herein by an amino acid sequence alignment, as provided in the figures.

FIGS. 1A and 1B provide an amino acid sequence alignment of the 5'-nuclease domains of Tma DNA polymerase and seven representative Thermus species DNA polymerases. The seven representative Thermus species DNA polymerases are listed in the table below, along with the abbreviations used herein and the sequence identification numbers for the amino acid sequences of the 5'-nuclease domains.

| Abbreviation | Species | Sequence of the 5'-Nuclease Domain |
|---|---|---|
| Tma | *Thermatoga maritima* | (SEQ ID NO: 1) |
| Taq | *Thermus aquaticus* | (SEQ ID NO: 2) |
| Tfl | *Thermus flavus* | (SEQ ID NO: 3) |
| Tth | *Thermus thermophilus* | (SEQ ID NO: 4) |
| TZ05 | *Thermus species* Z05 | (SEQ ID NO: 5) |
| Tca | *Thermus caldofilus* | (SEQ ID NO: 6) |
| Tsps17 | *Thermus species* sps17 | (SEQ ID NO: 7) |
| Tfi | *Thermus filiformis* | (SEQ ID NO: 8) |

The correspondence of amino acids and regions within these DNA polymerases is obtained from the amino acid sequence alignment. As used herein, amino acids "correspond" if they are aligned in the sequence alignment of FIGS. 1A and 1B. Thus, correspondence refers both to amino acids which are identical (conserved) among the sequences and to amino acids which are not identical, but which are aligned to maximize overall sequence homology.

A number of additional species of the genus Thermus have been identified and are available from depositories such the American Type Culture Collection (ATCC) and the Deutsche Sammlung von Mikroorganismen (DSM). As discussed below, DNA polymerases and the encoding genes can be recovered from the deposited strains and sequenced in a routine manner. A routine sequence alignment of the amino acid sequence of a Thermus species DNA polymerase sequence with the Tma DNA polymerase sequence using, for example, the GAP program, will enable the use of the Thermus DNA polymerase sequence in a chimeric DNA polymerase of the present invention.

In the chimeric protein of the invention, the first amino acid of the region from Tma DNA polymerase will begin with the amino acid following the amino acid that corresponds to the last amino acid of the Thermus species DNA polymerase sequence and will contain the rest (through amino acid 893) of the Tma DNA polymerase sequence. The sequence of the entire Tma DNA polymerase is provided as SEQ ID NO: 10. Preferably, the amino acid sequence from the Thermus species DNA polymerase is joined to an amino acid sequence from Tma DNA polymerase at a point where the two amino acid sequences are identical or similar. For example, a preferred embodiment consists of amino acids 1–190 from Taq DNA polymerase and amino acids 191–893 of Tma DNA polymerase. Amino acid 190 of Tma DNA polymerase corresponds to amino acid 190 of Taq DNA polymerase, and the Tma DNA polymerase portion of the chimeric enzyme begins with the next amino acid, amino acid 191.

In regions where the two DNA polymerases are identical, identification of the last amino acid from the Thermus species DNA polymerase is arbitrary within the region. For example, because amino acids 191 and 192 are identical in Taq DNA polymerases and Tma DNA polymerases (and conserved among Thermus species DNA polymerase), a chimeric protein that contains amino acids 1–190 of Taq DNA polymerase is indistinguishable from chimeric proteins containing amino acids 1–191 or 1–192 of Taq DNA polymerase. The embodiment of the invention described in the examples is referred to as containing amino acids 1–190 of Taq DNA polymerase in view of the original derivation of the enzyme.

In the sequence alignment provided in FIGS. 1A and 1B, gaps one amino acid in length were inserted into the Tma DNA sequence at positions 54–55 and 225–226 to allow alignment with five of seven of the Thermus species DNA polymerases which contain an additional amino acid at these positions. Consequently, for these two amino acids present in these five Thermus species, there are no corresponding amino acids in Tma DNA polymerase. One of skill in the art will realize that a suitable chimeric protein containing a N-terminal region from one of these five Thermus species DNA polymerases that ends with an amino acid which is aligned with a gap in Tma DNA polymerase can be constructed in which the Tma DNA polymerase-derived region starts at the first amino acid following the gap.

A critical aspect of the chimeric DNA polymerase is that it is encoded by a chimeric gene in which the region encoding the Tma DNA polymerase sequence through at least the alternative ribosomal binding site present at about codons 133–137 in the full-length Tma DNA polymerase gene, and preferably through the methionine140 start codon, is replaced by a gene sequence encoding the corresponding region from a Thermus species DNA polymerase. The presence in the full-length Tma DNA polymerase gene of this alternative ribosomal binding site and start codon results in the preferential expression of a truncated Tma DNA polymerase starting with amino acid 140. As described below, replacement of this region of the Tma DNA polymerase gene is critical to the efficient expression of the full-length chimeric protein. Thus, in the chimeric DNA polymerase of the invention, the N-terminal region from a Thermus species DNA polymerase replaces a region of Tma DNA polymerase that encompasses at least through amino acid 137, and preferably through amino acid 140.

The region of each Thermus species DNA polymerase that corresponds to amino acids 1–137 of Tma DNA polymerase is obtained from an amino acid sequence alignment, as provided in the figures. For example, the region of Taq DNA polymerase that corresponds to amino acids 1–137 of Tma DNA polymerase is amino acids 1–142 (see FIGS. 1A and 1B), and the amino acid of Taq DNA polymerase that corresponds M140 of Tma DNA polymerase is L145. Thus, embodiments in which the N-terminal region is from Taq DNA polymerase will comprise at least amino acids 1–142 and preferably, amino acids 1–145 of Taq DNA polymerase. Similarly, for embodiments in which the N-terminal region is from another Thermus species DNA polymerase, the region of the Thermus species DNA polymerase that corresponds to amino acids 1–137 and 140 of Tma DNA polymerase is obtained from the sequence alignment provided in the figures.

One of skill in the art will recognize that minor mutations, additions, or deletions can be introduced into a DNA polymerase that do not alter the functional properties of the enzyme, and that such a mutated enzyme is equivalent, for all intents and purposes, to the unmutated enzyme. For example, it is known that a deletion in Taq DNA polymerase of several N-terminal amino acids does not alter the functional properties of the enzyme. Similarly, it is known that substitution mutations at many of the amino acid positions appear to have essentially no affect. For the purposes of the present invention, DNA polymerases which contain minor mutations that do not alter the functional properties of the enzyme are considered to be equivalent to the unmutated DNA polymerase.

2. Point Mutations in the 5'-nuclease Domain

In one embodiment, the 5'-nuclease domain of the chimeric DNA polymerase contains one or more point mutations (single amino acid substitution or deletion mutations) which reduce or eliminate the 5'-nuclease activity. Because the 5'-nuclease domain of the chimeric protein contains portions derived from a Thermus species DNA polymerase and, in most embodiments, from Tma DNA polymerase, mutations which substantially reduce or eliminate the 5'-nuclease activity may be introduced either into the Thermus species DNA polymerase-derived portion or the Tma DNA polymerase-derived portion.

Based on amino acid sequence alignments, DNA polymerases have been classified into groups, designated families A, B, and C, according to the homology with *E. coli* DNA polymerases I, II, and III (see, for example, Ito and Braithwaite, *Nucl. Acids Res.* 19(15):4045–4–47, incorporated herein by reference). The Tma and Thermus species DNA polymerases are members of the family A DNA polymerases, which are related to *E. coli* DNA polymerase I. Amino acids which are conserved among family A DNA polymerases and which are critical to 5'-nuclease activity of the DNA polymerases have been identified (see, for example, Gutman et al. 1993, *Nucl. Acids. Res.* 21:4406–4407, incorporated herein by reference). Because of the conservation of amino acids which are critical for 5'-nuclease activity in family A DNA polymerases, the identification of critical amino acids in one DNA polymerase, such as *E. coli* DNA polymerase I or Taq DNA polymerase, allows identification of critical amino acids in other family A DNA polymerases based on a sequence alignment, such as provided in FIGS. 1A and 1B. Critical amino acids can be identified in additional Thermus species DNA polymerases from a routine sequence alignment with the sequences provided herein.

Amino acids that have been identified as critical to 5'-nuclease activity are indicated in FIGS. 1A and 1B with an asterisk. The positions of the critical amino acids within each DNA polymerase is obtained from the alignment. For example, referring the Taq DNA polymerase sequence, (SEQ ID NO: 2), these critical amino acids are as follows: D18, R25, G46, D67, F73, R74, Y81, G107, E117, D119, D120, D142, D144, G187, D188, D191, and G195.

It would not be surprising if additional critical amino acids are identified in the future. As mutations at these amino acid positions as described herein would result in a reduction or eliminating of the 5'-nuclease activity, such mutations would be suitable for use in the present invention.

In general, to reduce or eliminate 5'-nuclease activity, one or more of these amino acid positions is either deleted or mutated to an amino acid having a different property. For example, an acidic amino acid such as Asp (D) may be changed to a basic (Lys, Arg, His), neutral (Ala, Val, Leu, Ile, Pro, Met, Phe, Trp), or polar but uncharged amino acid (Gly, Ser, Thr, Cys, Tyr, Asn, or Gln). The preferred G46D mutation substitutes the acidic Asp for the polar but uncharged Gly. In general, mutations to Ala or Gly are preferable to minimize distortion of the protein structure.

Substitution mutations which preserve the charge property of the amino acid also may attenuate the 5'-nuclease activity. For example, U.S. Pat. No. 5,474,920, incorporated herein by reference, describes three mutations in the Taq DNA sequence which reduce or eliminate the 5'-nuclease activity. Although one of the mutations, R25C (basic to polar but uncharged), results in a change to an amino acid having a different property, two of the mutations, F73L (neutral to neutral) and R74H (basic to basic), do not result in a change in property. Nevertheless, all three mutations attenuate the 5'-nuclease activity. Particular mutations at each critical amino acid position which affect the 5'-nuclease activity can be determined routinely by mutating the DNA polymerase and measuring the resulting activity. A sensitive and convenient assay is described in U.S. Pat. No. 5,466,591, incorporated herein by reference.

In a preferred embodiment, the 5'-nuclease domain of the chimeric DNA polymerase contains a mutation corresponding to a G46D mutation in Taq DNA polymerase, which reduces the 5'-nuclease activity at least 1000-fold (see U.S. Pat. No. 5,466,591).

Mutations in the amino acid sequence are achieved by incorporating appropriate mutations in the encoding gene sequence. Such mutations in the DNA sequence are carried out using techniques well known in the art, as described further, below.

3. Point Mutations in the 3' to 5' Exonuclease Domain

In one embodiment, the 3' to 5' exonuclease domain of the chimeric DNA polymerase contains one or more point mutations (single amino acid substitution or deletion mutations) which reduce or eliminate the 3' to 5' exonuclease activity. The 3' to 5' exonuclease domain of the chimeric protein is contained within the Tma DNA polymerase-derived portion. Thus, suitable mutations are those which substantially reduce or eliminate the 5'-nuclease activity of Tma DNA polymerase.

Three amino acid "motifs" critical for 3' to 5' exonuclease activity in Tma DNA polymerase, along with the critical amino acids within each motif, have been identified (see U.S. Pat. No. 5,420,029). The critical amino acids are listed below. Mutations of one or more of these amino acids which reduce the 3' to 5' exonuclease activity in Tma DNA polymerase may be used in the DNA polymerases of the present invention.

| Tma DNA polymerase Amino Acids Critical to 3' to 5' exonuclease Activity | |
|---|---|
| Motif | Critical Amino acids |
| A | D323, E325, L329 |
| B | N385, D389, L393 |
| C | Y464, D468 |

It would not be surprising if additional critical amino acids are identified in the future. As mutations at these amino acid positions as described herein would result in a reduction or eliminating of the 3' to 5' exonuclease activity, such mutations would be suitable for use in the present invention.

As described above for the reduction of 5'-nuclease activity, reduction or elimination of 3' to 5' exonuclease activity is achieved by a substitution or deletion mutation at one or more of these critical amino acid positions, preferably a substitution mutation to an amino acid having a different property. In the preferred embodiment, the 3' to 5' exonuclease domain of Tma DNA polymerase is mutated by D323A and E325A mutations, which together essentially eliminate the 3' to 5' exonuclease activity.

Mutations in the amino acid sequence are achieved by incorporating appropriate mutations in the encoding gene sequence. Such mutations in the DNA sequence are carried out using techniques well known in the art, as described further, below.

Advantages of the DNA Polymerase of the Invention

The chimeric thermostable DNA polymerase of the invention represents a significant improvement over thermostable DNA polymerases described in the literature. In particular, the DNA polymerase of the invention provides the following combination of properties:

1. improved incorporation of ddNTPs;
2. improved uniformity of peak heights in DNA sequencing traces, in particular when used with dye-labeled ddNTPs in a cycle sequencing reaction;
3. reduced rate of pyrophosphorolysis of dye-labeled ddNTPs; and
4. improved incorporation of dITP.

Furthermore, (5) the DNA polymerase can be easily and efficiently expressed to a high level in a recombinant expression system, thereby facilitating commercial production of the enzyme.

The combination of properties possessed by the DNA polymerase of the invention is particularly useful in dye-terminator cycle sequencing reactions, and provides significantly improved results. Each of these properties is discussed below.

1. Improved Incorporation of ddNTPs

The chimeric DNA polymerase of the present invention contains the F730Y mutation, which is known to increase the efficiency of incorporation of ddNTPs.

By comparison, AmpliTaq® DNA polymerase, FS is a mutated form of Taq DNA polymerase that contains the analogous mutation (F667Y). AmpliTaq® DNA polymerase, FS also exhibits an increased efficiency of incorporation of ddNTPs, but lacks several the other properties exhibited by the DNA polymerase of the present invention.

2. Improved Uniformity of Peak Heights in DNA Sequencing Traces

An advantageous property of the DNA polymerase of the present invention is that, when used in a dye-terminator cycle sequencing reaction, it results in uniform peak heights in the sequencing trace (also referred to as chromatograms or electropherograms). Uneven peak heights can decrease the accuracy of base calling and make mutation and polymorphism detection more difficult.

Unevenness of peak heights in dye-terminator cycle sequencing reactions is a problem that previously had not been solved. For example, although AmpliTaq® DNA Polymerase, FS incorporates ddNTPs more efficiently than does unmutated Taq DNA polymerase, the peak height patterns obtained in dye-terminator sequencing reactions are uneven (see Parker et al., 1996, *BioTechniques* 21(4):694–699, incorporated herein by reference). The unevenness results at least partially from a dependence of peak height on the sequence context. For example, the peak height obtained from a G following an A can be extremely small, making an accurate base call difficult. Conversely, the peak height obtained from an A following an G can be very high. Particularly problematical patterns include G after A or C, A after A or C, and T after T, which can result in very low peak heights. Very high peak heights, such as results from A after G, are less problematical alone, but can render adjacent low signals unreadable.

As shown in the examples, the use of the chimeric DNA polymerase of the invention in cycle sequencing reactions results in significantly more uniform peak heights than obtained using AmpliTaq® DNA Polymerase, FS. The improved uniformity in peak height results in a significant increase in the accuracy of base calling and makes mutation and polymorphism detection easier.

3. Reduced Rate of Pyrophosphorolysis of Dye-labeled ddNTPs

DNA polymerases catalyze the template-dependent incorporation of a deoxynucleotide onto the 3'-hydroxyl terminus of a primer, with the concomitant release of inorganic pyrophosphate (PPi). This polymerization reaction is reversible. DNA polymerases also catalyze the reverse reaction, pyrophosphorolysis, which is the degradation of DNA in the presence of PPi. The reaction is summarized below:

$DNA_n + dNTP \leftarrow\!\!\rightarrow DNA_{n+1} + PPi$

Inorganic pyrophosphatase (PPase), also known as pyrophosphate phosphohydrolase, catalyzes hydrolysis of inorganic pyrophosphate (PPi) to two molecules of orthophosphate. PPase plays an vital role in RNA and DNA synthesis in vivo. By cleaving PPi, the enzyme shifts the overall equilibrium in favor of synthesis.

Pyrophosphorolysis can be detrimental to DNA sequencing reactions. Accuracy in DNA sequencing reactions depends on precise band position, a decrease in size of only one nucleotide can result in gel artifacts such as reduced or missing bands. Pyrophosphorolysis results in the removal of bases from the 3'-end of the primer extension product. Furthermore, removal of the incorporated terminal ddNMP (dideoxynucleosidemonophosphate) from a ddNMP-terminated fragment allows subsequent extension, which leads to signal strength reduction at the affected position and a reduced or missing peak in the electropherogram.

Thus, it is desirable to minimize the pyrophosphorolysis reaction in sequencing reactions. The addition of PPase to the reaction shifts the overall equilibrium in favor of synthesis by cleaving PPi. The use of PPase to improve sequencing reactions is described in Tabor and Richardson, 1990, J. Biol. Chem. 265(14):8322–8328; and in PCT Patent Publication No. WO 90/12111; both incorporated herein by reference. The commercially available cycle sequencing kits from Perkin Elmer (Norwalk, Conn.), which contain AmpliTaq® DNA Polymerase, FS, contain PPase to reduce pyrophosphorolysis.

Surprisingly, cycle sequencing reactions using the DNA polymerase of the present invention are much less affected by pyrophosphorolysis of the dye-labeled ddNTP terminators. As described in the examples, cycle sequencing reactions carried out with a range of PPase concentrations from 0 to 20 units yielded essentially identical results. Thus, the DNA polymerase of the present invention appears to greatly reduce or eliminate the need for PPase in cycle sequencing reactions.

4. Improved Incorporation of dITP

In a typical cycle sequencing reaction, dITP is used instead of dGTP in order to relieve compressions in G/C-rich regions. Incorporation of dITP into DNA reduces the denaturation temperature and facilitates denaturation of secondary structure. Because DNA polymerases discriminate against dITP, which is an unconventional nucleotide, the relative concentration of dITP must be substantially increased in a reaction to obtain adequate incorporation. For example, in the reaction conditions optimized for AmpliTaq® DNA Polymerase, FS, dITP is present at a concentration five-fold greater than the concentrations of dATP, dCTP, and dTTP.

In contrast, the DNA polymerase of the present invention incorporates dITP more efficiently, which allows the reaction to be carried out with more uniform dNTP concentrations. As described in the examples, a dITP concentration of only about two- to three-fold greater than the concentrations of dATP, dCTP, and dTTP is optimal for the DNA polymerase of the present invention.

5. Efficiency of Expression

As described above, the chimeric enzyme of the present invention corresponds to a mutated Tma DNA polymerase, wherein the 5'-nuclease domain has been replaced by the corresponding domain from a Thermus species DNA polymerase. The enzyme is expressed from a chimeric gene which corresponds to a mutated Tma DNA polymerase gene, wherein the region of the gene that encodes the 5'-nuclease domain has been replaced by the corresponding region of the Thermus species DNA polymerase gene. A significant advantage of the chimeric gene is that it enables the expression of a full-length DNA polymerase in a recombinant expression system much more efficiently than is possible from the Tma DNA polymerase gene.

The expression of a full-length DNA polymerase from a recombinant expression system containing the full-length natural Tma DNA polymerase gene sequence is problematical because of the preferential expression of a truncated form of the protein (see U.S. Pat. No. 5,420,029). The truncated protein, referred to as Met140 Tma, consists of amino acids 140–893 of the full-length protein and appears to result from translation beginning at the methionine at position 140. The presence of a putative ribosomal binding site at codons 133–137 further suggests that the truncated protein results from translation beginning at the internal methionine. The preferential expression of the Met140 Tma truncated protein represents a significant difficulty in expressing and purifying a full-length Tma DNA polymerase.

The chimeric DNA polymerase gene contains a Thermus species DNA polymerase gene sequence in a region corresponding at least through the alternative ribosomal binding site present at about codons 133–137 in the full-length Tma DNA polymerase gene, and preferably through the internal start codon, codon 140. Thus, the Tma DNA polymerase gene sequence up through the region containing the ribosomal binding site and, preferably, the start codon responsible for the translation of Met140 Tma, is replaced by the corresponding region of a Thermus species DNA polymerase gene. The corresponding region of a Thermus species DNA polymerase gene does not provide for the undesirable internal initiation of a truncated protein. As a result, a recombinant expression system containing the chimeric DNA polymerase gene expresses a full-length chimeric DNA polymerase exclusively.

Preparation of the DNA Polymerase of the Invention

The DNA polymerase of invention is a chimeric enzyme that consists of a portion derived from a Thermus species DNA polymerase and a portion derived from Tma DNA polymerase. The chimeric enzyme is prepared from a chimeric gene, i.e., a DNA that encodes the chimeric enzyme and consists of a portion derived from the Thermus species DNA polymerase gene and a portion derived from the Tma DNA polymerase gene. The chimeric gene is produced from the Thermus species DNA polymerase gene and the Tma DNA polymerase gene using standard gene manipulation techniques well known in the field of molecular biology, as described in detail below.

The gene encoding Tma DNA polymerase is described in U.S. Pat. Nos. 5,420,029 and 5,466,591. The nucleotide sequence of the Tma DNA polymerase gene, as well as the full amino acid sequence of the encoded protein, are described therein. Example 5 of the '029 patent describes the construction of a variety of plasmids containing the full-length Tma DNA polymerase gene starting with plasmids pTma01 (ATCC No. 68471, deposited Nov. 7, 1990, and redeposited as ATCC No. 98764 on May 22, 1998) and pTma04 (ATCC No. 68472, deposited Nov. 7, 1990, and redeposited as ATCC No. 98765 on May 22, 1998), such as plasmids pTma12-1 and pTma13. Any of these expression vectors is suitable as a source of the Tma DNA polymerase gene.

Genes encoding DNA polymerases from a number of Thermus species, including the nucleotide sequence of the DNA polymerase gene and the amino acid sequence of the encoded protein, have been described. A number of these genes are obtainable from publicly available plasmids. The genes from additional Thermus species are obtainable from the host organisms using methods described in U.S. Pat. Nos. 5,079,352; 5,618,711; 5,455,170; 5,405,774; and 5,466,591; each incorporated by reference.

The gene encoding Taq DNA polymerase is described in U.S. Pat. Nos. 5,079,352 and 5,466,591. The nucleotide sequence of the Taq DNA polymerase gene, as well as the full amino acid sequence of the encoded protein, are described therein. Examples V–VII of the '352 patent describes the construction of a variety of expression plasmids containing the full-length Taq DNA polymerase gene starting with plasmids pFC83 (ATCC No. 67422, deposited on May 29, 1987, and redeposited as ATCC No. 98763 on May 22, 1998) and pFC85 (ATCC No. 67421, deposited May 29, 1987, and redeposited as ATCC No. 98762 on May 22, 1998), such as plasmids pLSP1, pLSG2, pSYC1578, pLSG5, and pLSG6. Any of these expression vectors is suitable as a source of the Taq DNA polymerase gene.

The gene encoding Tth DNA polymerase, methods for obtaining the gene, and expression plasmids containing the gene are described in U.S. Pat. Nos. 5,618,711 and 5,466,591.

The gene encoding TZ05 DNA polymerase, methods for obtaining the gene, and expression plasmids containing the gene are described in U.S. Pat. Nos. 5,455,170 and 5,466,591.

The gene encoding Tsps17 DNA polymerase, methods for obtaining the gene, and expression plasmids containing the gene are described in U.S. Pat. Nos. 5,405,774 and 5,466,591.

The Tfl DNA polymerase gene is described in Akhmetz-janov and Vakhitov, 1992, *Nucleic Acids Research* 20(21):5839, incorporated herein by reference.

The Tfi DNA polymerase gene can be recovered from ATCC 43280 using the methods described in the referenced patents (see also 1984, FEMS *Microbiol. Lett.* 22:149–153 (1984)).

The Tca DNA polymerase gene is described in Kwon, 1997, *Mol. Cells* 7(2): 264–271; and the nucleotide sequence is available under EMBL/GenBank Accession No. U62584.

Additional Thermus species DNA polymerase genes can be recovered using techniques described in the above cited patents from the following ATCC deposits: ATCC 43814 and 43815 (see Alfredsson, 1986, *Appl. Environ. Microbiol.* 52:1313–1316); ATCC 27978 (see Ramaley, 1970, *J. Bacteriol.* 114:556–562; 1973; ibid. 103:527–528); ATCC 31674 (see U.S. Pat. Nos. 4,442,214 and 4,480,036); ATCC 35948 (*T. ruber*, see Loginova, 1984, *Int. J. Syst. Bacteriol.* 34:498–499). All references are incorporated herein by reference.

Additional Thermus species can be recovered using techniques described in the above cited patents from the following Deutsche Sammlung von Mikroorganismen (DSM) deposits: DSM:1279 (NUM: 2244) (see Loginova, et al., 1975, *Izv. Akad. Nauk SSSR Ser. Biol.*: 304–307); DSM:579; DSM:625 (NUM: 2248) (see Degryse et al., 1978, *Arch. Microbiol.* 189:196); DSM:1279 (NUM: 3844) (see Loginova et al., 1984, *Int. J. Syst. Bacteriol.*:498–499); and DSM:625(NUM: 1002) (see Brock and Freeze, 1969, *J. Bacteriol.*:289–297). All references are incorporated herein by reference.

Additional Thermus species which have been described include *T. oshimai* (see Williams et al., 1996, *Int. J. Syst. Bacteriol.* 46(2):403–408); *T. silvanus* and *T. chliarophilus* (see Tenreiro et al. 1995, *Int. J. Syst. Bacteriol.* 45(4):633–639); *T. scotoductus* (see Tenreiro et al., 1995, *Res. Microbiol.* 146(4):315–324); and *T. ruber* (see Shadrina et al., 1982, *Mikrobiologiia* 51(4):611–615); all incorporated herein by reference.

Following the guidance provided herein, and using only well known techniques, one skilled in the art will be able to prepare from the DNA polymerase genes any number of expression vectors containing a chimeric gene suitable for expressing the chimeric DNA polymerases of the invention in any of a variety of host systems.

In a preferred embodiment, the chimeric enzyme of the invention consists of amino acids 1–190 from Taq DNA polymerase and amino acids 191–893 from Tma DNA polymerase, both regions suitably mutated to eliminate associated exonuclease activity. This preferred embodiment can be constructed directly from the Taq DNA polymerase and Tma DNA polymerase genes, either obtained from the deposited plasmids described above or recovered from the host organisms. However, such chimeric DNA polymerases can be most easily constructed from plasmid pUC18:Tma25, which was deposited with the ATCC under accession No. 98443 on May 28, 1997.

Plasmid pUC18:Tma25 contains a chimeric gene that encodes a chimeric protein consisting of amino acids 1–190 from Taq DNA polymerase and amino acids 191–893 of Tma DNA polymerase. The chimeric protein encoded by pUC18:Tma25 contains the G46D mutation in the Taq DNA polymerase portion. The nucleotide sequence of the chimeric gene of pUC18:Tma25 is provided as SEQ ID NO: 9.

Suitable expression systems are constructed from pUC18:Tma25 by sub-cloning the chimeric gene into a suitable expression vector, introducing one or more point mutations which attenuate or eliminate the 3' to 5' exonuclease activity of the encoded protein, and introducing the F730Y mutation in the Tma DNA polymerase portion. The construction of a preferred expression system, which encodes a chimeric protein containing a G46D mutation in 5'-nuclease domain, D323A and E325A mutations in the 3' to 5' exonuclease domain, and a F730Y mutation in the Tma DNA polymerase portion, is described in the examples.

The nucleotide sequence of pUC18:Tma25 that encodes amino acids 1–190 of Taq DNA polymerase was derived from plasmid pRDA3-2, described in U.S. Pat. No. 5,466,591, and, thus, encodes an amino acid sequence containing the G46D mutation described therein. The nucleotide sequence of pRDA3-2 and, hence, pUC18:Tma25, also contains additional mutations relative to the native Taq DNA polymerase gene sequence (SEQ ID NO: 9) which are silent, i.e., do not alter the amino acid sequence encoded.

Because of the redundancy in the genetic code, typically a large number of DNA sequences encode any given amino acid sequence and are, in this sense, equivalent. As described below, it may be desirable to select one or another equivalent DNA sequences for use in a expression vector, based on the preferred codon usage of the host cell into which the expression vector will be inserted. The present invention is intended to encompass all DNA sequences which encode the chimeric enzyme. Thus, chimeric genes of the present invention are not limited to containing only sequences from the wild-type Thermus species and Tma DNA polymerase genes, but can contain any of the DNA sequences which encode a chimeric DNA polymerase of the present invention.

Production of the enzyme of the invention is carried out using a recombinant expression clone. The construction of the recombinant expression clone, the transformation of a host cell with the expression clone, and the culture of the transformed host cell under conditions which promote expression, can be carried out in a variety of ways using techniques of molecular biology well understood in the art. Methods for each of these steps are described in general below. Preferred methods are described in detail in the examples.

An operable expression clone is constructed by placing the coding sequence in operable linkage with a suitable control sequences in an expression vector. The vector can be designed to replicate autonomously in the host cell or to integrate into the chromosomal DNA of the host cell. The resulting clone is used to transform a suitable host, and the transformed host is cultured under conditions suitable for expression of the coding sequence. The expressed protein is isolated from the medium or from the cells, although recovery and purification of the protein may not be necessary in some instances.

Construction of suitable clones containing the coding sequence and a suitable control sequence employs standard ligation and restriction techniques that are well understood in the art. In general, isolated plasmids, DNA sequences, or synthesized oligonucleotides are cleaved, modified, and religated in the form desired. Suitable restriction sites can, if not normally available, be added to the ends of the coding sequence so as to facilitate construction of an expression clone.

Site-specific DNA cleavage is performed by treating with a suitable restriction enzyme (or enzymes) under conditions that are generally understood in the art and specified by the manufacturers of commercially available restriction enzymes. See, e.g., product catalogs from Amersham (Arlington Heights, Ill.), Boehringer Mannheim (Indianapolis, Ind.), and New England Biolabs (Beverly, Mass.). In general, about 1 $\mu$g of plasmid or other DNA is cleaved by one unit of enzyme in about 20 $\mu$l of buffer solution; in the examples below, an excess of restriction enzyme is generally used to ensure complete digestion of the DNA. Incubation times of about one to two hours at a temperature which is optimal for the particular enzyme are typical. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., Maxam et al., *Methods in Enzymology*, 1980, 65:499–560.

Restriction-cleaved fragments with single-strand "overhanging" termini can be made blunt-ended (double-strand ends) by treating with the large fragment of *E. coli* DNA polymerase I (Klenow) in the presence of the four deoxynucleoside triphosphates (dNTPs) using incubation times of about 15 to 25 minutes at 20° C. to 25° C. in 50 mM Tris, pH 7.6, 50 mM NaCl, 10 mM MgCl$_2$, 10 mM DTT, and 5 to 10 $\mu$M dNTPs. The Klenow fragment fills in at 5' protruding ends, but chews back protruding 3' single strands, even though the four dNTPs are present. If desired, selective repair can be performed by supplying one or more selected dNTPs, within the limitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Ligations are performed in 15–30 $\mu$l volumes under the following standard conditions and temperatures: 20 mM Tris-Cl, pH 7.5, 10 mM MgCl$_2$, 10 mM DTT, 33 $\mu$g/ml BSA, 10–50 mM NaCl, and either 40 $\mu$M ATP and 0.01–0.02 (Weiss) units T4 DNA ligase at 0° C. (for ligation of fragments with complementary single-stranded ends) or 1 mM ATP and 0.3–0.6 units T4 DNA ligase at 14° C. (for "blunt end" ligation). Intermolecular ligations of fragments with complementary ends are usually performed at 33–100 $\mu$g/ml total DNA concentrations (5–100 nM total ends concentration). Intermolecular blunt end ligations (usually employing a 20–30 fold molar excess of linkers, optionally) are performed at 1 $\mu$M total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove the phosphatase and purify the DNA. Alternatively, religation of unwanted vector fragments can be prevented by restriction enzyme digestion before or after ligation, if appropriate restriction sites are available.

In the construction set forth below, correct ligations for plasmid construction are confirmed by first transforming a suitable host, such as *E. coli* strain DG101 (ATCC 47043) or *E. coli* strain DG116 (ATCC 53606), with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, *Proc. Natl. Acad. Sci. USA* 62:1159, optionally following chloramphenicol amplification (Clewell, 1972, *J. Bacteriol.* 110:667). Alternatively, plasmid DNA can be prepared using the "Base-Acid" extraction method at page 11 of the Bethesda Research Laboratories publication *Focus* 5 (2), and very pure plasmid DNA can be obtained by replacing steps 12 through 17 of the protocol with CsCl/ethidium bromide ultracentrifugation of the DNA. The isolated DNA is analyzed by restriction enzyme digestion and/or sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of the protein.

The procaryote most frequently used to express recombinant proteins is *E. coli*. However, microbial strains other than *E. coli* can also be used, such as bacilli, for example *Bacillus subtilis*, various species of Pseudomonas, and other bacterial strains, for recombinant expression of the protein. In such procaryotic systems, plasmid vectors that contain replication sites and control sequences derived from the host or a species compatible with the host are typically used.

For expression of constructions under control of most bacterial promoters, *E. coli* K12 strain MM294, obtained from the *E. coli* Genetic Stock Center under GCSC #6135, can be used as the host. For expression vectors with the $P_L N_{RBS}$ or $P_L T7_{RBS}$ control sequence, *E. coil* K12 strain MC1000 lambda lysogen, $N_7 N_{53}$cI857 SusP$_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98 (ATCC 39768), are employed. The DG98 strain was deposited with the ATCC on Jul. 13, 1984.

For example, *E. coli* is typically transformed using derivatives of pBR322, described by Bolivar et al., 1977, *Gene* 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems (Chang et al., 1977, *Nature* 198:1056), the tryptophan (trp) promoter system (Goeddel et al., 1980, *Nuc. Acids Res.* 8:4057), and the lambda-derived $P_L$ promoter (Shimatake et al., 1981, *Nature* 292:128) and gene N ribosome binding site ($N_{RBS}$). A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six base pairs 3' of the $N_{RBS}$ sequence. Also useful is the phosphatase A (phoA) system described by Chang et al., in European Patent Publication No. 196,864, published Oct. 8, 1986. However, any available promoter system compatible with procaryotes can be used to construct a expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101:307), other plasmid vectors suitable for yeast expression are known (see, for example, Stinchcomb et al., 1979, *Nature* 282:39; Tschempe et al., 1980, *Gene* 10:157; and Clarke et al., 1983, *Meth. Enz.* 101:300). Control sequences for yeast vectors include promoters for the synthesis of glycolytic enzymes (Hess et al., 1968, *J. Adv. Enzyme Reg.* 7:149; Holland et al., 1978, *Biotechnology* 17:4900; and Holland et al., 1981, *J. Biol. Chem.* 256:1385). Additional promoters known in the art include the promoter for 3-phosphoglycerate kinase (Hitzeman et al., 1980, *J. Biol. Chem.* 255:2073) and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast expression vectors.

The coding sequence can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113), or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1:561) are available. Expression systems employing insect cells utilizing the control systems provided by baculovirus vectors have also been described (Miller et al., in *Genetic Engineering* (1986), Setlow et al., eds., Plenum Publishing, Vol. 8, pp. 277–297). Insect cell-based expression can be accomplished in *Spodoptera frugipeida*. These systems are also successful in producing recombinant enzymes.

Depending on the host cell used, transformation is done using standard techniques appropriate to such cells. The calcium treatment employing calcium chloride, as described by Cohen, 1972, *Proc. Natl. Acad. Sci. USA* 69:2110 is used for procaryotes or other cells that contain substantial cell wall barriers. Infection with *Agrobacterium tumefaciens*

(Shaw et al., 1983, *Gene* 23:315) is used for certain plant cells. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946, and Hsiao et al., 1979, *Proc. Natl. Acad. Sci. USA* 76:3829.

It may be desirable to modify the sequence of the DNA encoding the enzyme of the invention to provide, for example, a sequence more compatible with the codon usage of the host cell without modifying the amino acid sequence of the encoded protein. Such modifications to the initial 5–6 codons may improve expression efficiency. DNA sequences which have been modified to improve expression efficiency, but which encode the same amino acid sequence, are considered to be equivalent and encompassed by the present invention.

A variety of site-specific primer-directed mutagenesis methods are available and well-known in the art (see, for example, Sambrook et al., Molecular Cloning: A Laboratory Manual, Cold Spring Harbor, 1989, second edition, chapter 15.51, "Oligonucleotide-mediated mutagenesis," which is incorporated herein by reference). The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence contained in a single-stranded vector, such as pBSM13+ derivatives, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

Once the protein has been expressed in a recombinant host cell, purification of the protein may be desired. A variety of purification procedures can be used to purify the recombinant thermostable DNA polymerase of the invention. Examples include the methods for purifying Taq DNA polymerase described in U.S. Pat. Nos. 4,889,818; 5,352,600; and 5,079,352; the methods for purifying the DNA polymerase from *Thermus thermophilis* (Tth) described in U.S. Pat. Nos. 5,618,711 and 5,310,652; the methods for purifying Tma DNA polymerase described in U.S. Pat. Nos. 5,374,553 and 5,420,029. Methods for purifying these DNA polymerases are also described in U.S. Pat. No. 5,466,591. All of the above patents are incorporated herein by reference.

In a preferred method, the expression of the DNA polymerase is carried out in *E. coli*, which is a mesophilic bacterial host cell. Because *E. coli* host proteins are heat-sensitive, the recombinant thermostable DNA polymerase can be substantially enriched by heat inactivating the crude lysate. This step is done in the presence of a sufficient amount of salt (typically 0.2–0.4 M ammonium sulfate) to reduce ionic interactions of the DNA polymerase with other cell lysate proteins.

Activity of the purified DNA polymerase is assayed as described in Lawyer et al., 1989, *J. Biol. Chem.* 264:6427, incorporated herein by reference.

For long-term stability, the purified DNA polymerase enzyme must be stored in a buffer that contains one or more non-ionic polymeric detergents. Such detergents are generally those that have a molecular weight in the range of approximately 100 to 250,00 preferably about 4,000 to 200,000 daltons and stabilize the enzyme at a pH of from about 3.5 to about 9.5, preferably from about 4 to 8.5. Examples of such detergents include those specified on pages 295–298 of McCutcheon's *Emulsifiers & Detergents*, North American edition (1983), published by the McCutcheon Division of MC Publishing Co., 175 Rock Road, Glen Rock, N.J. (USA), the entire disclosure of which is incorporated herein by reference. Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20™, a polyoxyethylated (20) sorbitan monolaurate from ICI Americas Inc. (Wilmington, Del.), and Iconol™ NP-40, an ethoxylated alkyl phenol (nonyl) from BASF Wyandotte Corp. (Parsippany, N.J.).

The thermostable enzyme of this invention may be used for any purpose in which a thermostable DNA polymerase is necessary or desired. In a preferred embodiment, the enzyme is for DNA sequencing (see Innis et al., 1988, *Proc. Natl. Acad. Sci. USA* 85:9436–9440, incorporated herein by reference).

The following examples are offered by way of illustration only and are by no means intended to limit the scope of the claimed invention. In these examples, all ercentages are by weight if for solids and by volume if for liquids, unless otherwise noted.

EXAMPLE 1

Construction of an Expression System

An expression system is constructed from the deposited plasmid, pUC18:Tma25, which contains the gene having nucleotide sequence SEQ ID NO: 9, using conventional techniques well known in the art. The steps involved, which are described in more detail below, are as follows.

I. The DNA polymerase coding sequence contained in pUC18:Tma25 is subcloned into a pDG1 60 expression vector, resulting in plasmid pTMA25.

II. The D323A and E325A mutations are added to pTMA25 by site-specific primer-directed mutagenesis, resulting in plasmid pTMA30.

III. The mutated gene coding sequence from pTMA30 is then subcloned into a pDG184 expression vector such that codons 1–283 are deleted, resulting in plasmid pTMA31.

IV. The F730Y mutation is added to pTMA31 by site-specific primer-directed mutagenesis, resulting in plasmid pTMA31[F730Y].

V. A fragment of the mutated coding sequence from pTMA31[F730Y] containing the F730Y mutation is subcloned into pTMA30 to replace the corresponding unmutated fragment, resulting in plasmid pTMA30 [F730Y].

Following each mutagenesis or sub-cloning step, *E. coli* strain DG116 host cells are transformed with the plasmid constructs. Ampicillin resistant (plasmid containing) colonies are screened for the presence of the desired plasmid using standard methods. Typically, first colonies are selected for the presence of a plasmid of the expected size by gel electrophoretic size fractionation. Candidate colonies are further screened for plasmids exhibiting the expected fragment pattern following digestion with one or more restriction enzymes. Finally, mutagenized sites and ligation junctions are sequenced to confirm the intended sequence.

Plasmid pDG160 is described in U.S. Pat. No. 5,618,711, incorporated herein by reference. Plasmid pDG160 is a cloning and expression vector that comprises the bacteriophage λ $P_L$ promoter and gene N ribosome binding site (see U.S. Pat. No. 4,711,845, incorporated herein by reference), a restriction site polylinker positioned so that sequences cloned into the polylinker can be expressed under the control of the λ $P_L$ promoter and gene N ribosome binding site, and a transcription terminator from the *Bacillus thuringiensis* delta-toxin gene (see U.S. Pat. No. 4,666,848, incorporated herein by reference). Plasmid pDG160 also carries a mutated RNAII gene, which renders the plasmid temperature sensitive for copy number (see U.S. Pat. No. 4,631,257, incorporated herein by reference).

These elements act in concert to make plasmid pDG160 a very useful and powerful expression vector. At 30–32° C., the copy number of the plasmid is low, and in an host cell that carries a temperature-sensitive λ repressor gene, such as cI857, the $P_L$ promoter does not function. At 37–41° C., however, the copy number of the plasmid is 50-fold higher than at 30–32° C., and the cI857 repressor is inactivated, allowing the $P_L$ promoter to function. Plasmid pDG160 also carries an ampicillin resistance (AmpR) marker. In summary, plasmid pDG160 comprises the AmpR marker, the λ $P_L$ promoter and gene N ribosome binding site, a polylinker, and the BT cry PRE (BT positive retroregulatory element, U.S. Pat. No. 4,666,848) in a ColE1 $cop^{ts}$ vector.

Plasmid pDG184 is described in U.S. Pat. No. 5,420,029, incorporated herein by reference. Plasmid pDG184 is a derivative of pDG160, modified to include an Nco I site at the start codon of the inserted gene. The rest of the plasmid is functionally unchanged from pDG160.

I. Sub-cloning I

The DNA polymerase coding sequence is subcloned from plasmid pUC18:Tma25 into a pDG160 expression plasmid as follows:

A. Plasmid pUC18:Tma25, a 5347 base pair (bp) plasmid, is linearized by digestion with Nsp V, which cuts once at position 2084 (numbered starting with the first nucleotide of the coding sequence).

B. The linearized plasmid resulting from the Nsp V digestion is digested further with Bam HI, which cuts at nucleotide (nt) positions 1661, 1989, 2039, and 2686. A 602 bp Nsp V/Bam HI fragment (nt 2085–2686) containing the 3' end of the DNA polymerase gene is gel purified.

C. In a separate reaction, linearized plasmid resulting from the Nsp V digestion is digested further with Hind III, which cuts at positions 2629 and 5342. A 2089 bp Nsp V/Hind III fragment (nt 5343–2084) containing the 5' end of the DNA polymerase gene is gel purified.

D. Plasmid pDG160 is digested with Hind III and Bam HI and treated with calf intestinal alkaline phosphatase (CIAP) to remove the 5' phosphate and prevent religation and reconstruction of the vector. Alternatively, the digested vector fragment is gel purified.

E. The isolated fragments from steps B and C are combined with the digested pDG160 plasmid from step D in a 2:2:1 ratio at a concentration of 10–40 ng/μl of total DNA and ligated, resulting in a 8218 bp plasmid.

D. The ligation product is transformed into *E. coli* DG116 cells (described above) and transformant colonies which contain the desired plasmid, designated pTMA25, are identified by screening.

II. Mutagenesis I: D323A and E325A

Mutations in the DNA polymerase coding sequence of pTMA25 which result in the D323A and E325A amino acid mutations are made using site-specific primer-directed mutagenesis. For convenience in later manipulations, additional mutations are made which eliminate a Bgl II restriction enzyme cleavage site and create an Spe I restriction enzyme cleavage site. These additional mutations are made such that the encoded amino acid sequence is unchanged.

The following primers are used in the mutagenesis.

1. Primer P1: mutagenic upstream primer corresponding to nucleotides 958–988 of SEQ ID NO: 9, with mutations as described in the table below.
2. Primer P2: mutagenic downstream primer consisting of the reverse complement of primer P1.
3. Primer P3: upstream primer corresponding to nucleotides 608–627 of SEQ ID NO: 9, which encompasses an Xba I site (nucleotides 621–626).
4. Primer P4: downstream primer corresponding to nucleotides 1319–1339 of SEQ ID NO: 9, which encompasses part of a Sac I site (nucleotides 1318–1323).

The sequence of mutagenic upstream primer P1 consists of nucleotides 958–988 of the coding strand of SEQ ID NO: 9, except for the changes shown in the table below. The change in codon 323 (nucleotides 967–969) resulted in the elimination of a Bgl II site. The changes in codons 326 (nucleotides 966–978) and 327 (nucleotides 979–981) do not affect the sequence of the encoded amino acid, but results in the creation of a Spe I site.

| Mutations in the primer P1 | | | |
|---|---|---|---|
| nucleotides | codon | nucleotide change | amino acid change |
| 967–969 | 323 | GAT -> GCT | D323A |
| 973–975 | 325 | GAG -> GCG | E325A |
| 976–978 | 326 | ACG -> ACT | none |
| 979–981 | 327 | TCT -> AGT | none |

The mutagenesis is carried out as described below. All amplifications are carried out by PCR under conditions well known in the art. For example, amplifications may be carried out using the GeneAmp PCR Reagent Kit with AmpliTaq® DNA Polymerase (Perkin Elmer, Norwalk, Conn.).

A. A region of the coding sequence is amplified from purified pTMA25 using primers P3 and P2, and the resulting 381 bp amplified product is gel purified.

B. A region of the coding sequence is amplified from purified pTMA25 using primers P1 and P4, and the resulting 382 bp amplified product is gel purified.

C. The amplified products from steps A and B are combined, heat denatured at 95° C., annealed, and extended with DNA polymerase using standard techniques.

D. The annealed and extended duplex DNA from step C is re-amplified using primers P3 and P4, and the resulting 732 bp amplified product is gel purified.

E. The amplified DNA from step D is digested with Xba I and Sac I.

F. Plasmid pTMA25 is digested with Xba I and Sac I, and treated with calf intestinal alkaline phosphatase (CIAP) to remove the 5' phosphate and prevent religation and reconstruction of the vector.

G. The digested DNA from step E is combined with the digested plasmid from step F in a 3:1 ratio and ligated.

H. The ligation product is transformed into *E. coli* DG116 cells and transformant colonies which contain the desired plasmid, designated pTMA30, are identified by screening.

III. Sub-cloning II

The mutated gene coding sequence from pTMA30 is then subcloned into a pDG184 expression vector such that codons 1–283 are deleted. Nucleotide position numbers used herein refer to the position within the plasmid, wherein position 1 is defined by the Eco RI site upstream of the λ $P_L$ promoter. The sub-cloning is carried out as follows.

A. Plasmid pTMA30, a 8218 bp plasmid, is digested with Mlu I, which cuts at nucleotide position 4443; Bsp HI, which cuts at positions 1210, 4761, 5769, and 5874; and Afl II, which cuts at position 7827. The Afl II digestion is carried out to further degrade a 3554 bp Bsp HI/Bsp HI fragment, which is similar in size to the desired 3233 bp Bsp HI/Mlu I fragment, in order to facilitate isolation of the desired fragment. The digestion yields six fragments, with lengths of 3233, 1952, 1601, 1008, 318, and 105 bp. The 3233 bp Bsp HI/Mlu I fragment corresponding to nucleotides 1211–4443 of the plasmid is isolated by gel electrophresis.

B. Plasmid pDG184, a 5474 bp plasmid, is digested with Mlu I, which cuts at position 1699, and Nco I, which cuts at position 284. The digested fragments are treated with calf intestinal alkaline phosphatase (CIAP) to remove the 5' phosphate and prevent religation and reconstruction of the vector. Alternatively, the 4059 bp fragment is isolated by gel electrophoresis.

C. The isolated fragment from step A is combined with the digested pDG184 plasmid from step B in a 1:1 ratio at a concentration of 10–40 ng/μl of total DNA and ligated, resulting in a 7292 bp plasmid.

D. The ligation product is transformed into $E. coli$ DG116 cells and transformant colonies which contain the desired plasmid, designated pTMA31, are identified by screening.

IV. Mutagenesis II: F730Y

Additional mutations in the DNA polymerase coding sequence of pTMA31 which resulted in the F730Y mutation in the encoded amino acid sequence mutations were made using site-specific primer-directed mutagenesis. The mutagenesis was carried out using methods analogous to those described above.

The following primers were used in the mutagenesis.
1. Primer FR1: mutagenic upstream primer corresponding to nucleotides 2173–2202 of SEQ ID NO: 9, with mutations as described in the table below.
2. Primer FR2: mutagenic downstream primer essentially consisting of the reverse complement of primer FR1, but corresponding to nucleotides 2172–2200 of SEQ ID NO: 9.
3. Primer FR3: upstream primer corresponding to nucleotides 1952–1972 of SEQ ID NO: 9, which lies upstream of a Bst XI site.
4. Primer FR4: downstream primer corresponding to nucleotides 2415–2433 of SEQ ID NO: 9, which lies downstream of a Xma I site.

The sequence of mutagenic upstream primer FRI consists of nucleotides 2173–2202 of the coding strand of SEQ ID NO: 9, except for the changes shown in the table below. The change in codons 729 (2185–2187) does not affect the sequence of the encoded amino acid, but results in the creation of a Hpa I site.

Mutations in the primer FR1

| nucleotides | codon | nucleotide change | amino acid change |
|---|---|---|---|
| 2185–2187 | 729 | AAT -> AAC | none |
| 2188–2190 | 730 | TTT -> TAT | F730Y |

The mutagenesis was carried out as described below.

A. A region of the coding sequence was amplified from purified pTMA31 using primers FR3 and FR2, and the resulting 249 bp amplified product was gel purified.

B. A region of the coding sequence was amplified from purified pTMA31 using primers FR1 and FR4, and the resulting 261 bp amplified product was gel purified.

C. The amplified products from steps A and B were combined, heat denatured at 95° C., annealed, and extended with DNA polymerase using standard techniques.

D. The annealed and extended duplex DNA from step C was re-amplified using primer FR3 and FR4, and the resulting 482 bp amplified product was extracted using a phenol/chloroform mixture and precipitated with EtOH.

E. The amplified DNA from step D was digested with Bst XI and Xma I, and the desired 337 bp DNA fragment was separated from smaller fragments using a CENTRICON 100 column (Amicon, Beverly, Mass.).

F. Plasmid pTMA31 was digested with Bst XI and Xba I.

G. The digested DNA from step E was combined with the digested plasmid from step F in a 3:1 ratio and ligated.

H. The ligation product was transformed into $E. coli$ DG116 cells. Colonies were screened for the presence of the desired mutated plasmid by amplifying the plasmid DNA using primers FR3 and FR4, which amplify a region encompassing the unique Hpa I site introduced during the mutagenesis, digesting the amplified product with Hpa I, and analyzing the digestion product by gel electrophoresis. A colony containing the desired plasmid, designated pTMA31 [F730Y], was selected and the gene sequence was confirmed by DNA sequencing.

The resulting expression system expresses a DNA polymerase, designated F730YTma31 DNA Polymerase, that consists of amino acids 284–893 of Tma DNA polymerase, mutated with the D323A, E325A, and F730Y mutations.

V Sub-cloning III

A fragment of the mutated coding sequence from pTMA31[F730Y] containing the F730Y mutation was subcloned into pTMA30 to replace the corresponding unmutated fragment, resulting in plasmid pTMA30[F730Y]. Nucleotide position numbers used herein refer to the position within the plasmid, wherein position 1 is defined by the Eco RI site upstream of the λ $P_L$ promoter. The sub-cloning was carried out as follows.

A. Plasmid pTMA31[F730Y], a 7292 bp plasmid, was digested with Mlu I, which cuts at nucleotide position 3517, and Spe I, which cuts at position 412. The 3105 bp Mlu I/Spe I fragment corresponding to nucleotides 413 to 3517 of the plasmid was isolated by gel electrophresis.

B. Plasmid pTMA30, a 8218 bp plasmid, is digested with Mlu I, which cuts at nucleotide position 4443, and Spe I, which cuts at position 1338. The 5113 bp Mlu I/Spe I fragment corresponding to nucleotides 4444–1338 of the plasmid fragment was isolated by gel electrophoresis.

C. The isolated fragment from step A is combined with the isolated fragment from step B in a 1:1 ratio at a concentration of 10–40 ng/μl of total DNA and ligated.

D. The ligation product was transformed into $E. coil$ DG116 cells. Colonies were screened for the presence of the desired 8.2 kb plasmid by amplifying the plasmid DNA using primers which amplify regions encompassing the unique Hpa I and Spe I sites introduced during the mutatageneses, digesting the amplified products with Hpa I or Spe I, and analyzing the digestion products by gel electrophoresis. Plasmid DNA was prepared from colonies that contained plasmids which exhibited the expected digestion pattern in the screen, and was further analyzed by digestion with Hpa I, Spe I, and Mlu I followed by gel analysis of the digested DNA. A colony containing the desired plasmid, designated pTMA30[F730Y], was selected and the gene sequence was confirmed by DNA sequencing.

The resulting expression plasmid, pTMA30[F730Y], is under the control of the bacteriophage λ $P_L$ promoter and gene N ribosome binding site, and a Positive Retroregulatory Element (PRE, transcription terminator) from the *Bacillus thuringiensis* delta-toxin gene. The plasmid also carries a mutated RNA II gene which renders the plasmid temperature sensitive for copy number and an ampicillin resistance gene.

EXAMPLE 2

Expression of the Recombinant DNA Polymerase

This example describes the expression and purification of F730YTma30 DNA Polymerase using an expression system, *E. coli* K12 strain DG116 cells harboring plasmid pTMA30 [F730Y], essentially as described in example 1.

Initial growth of the expression system cells was carried out in a seed flask. Large scale fermentation was carried out in a 10 liter fermentation flask inoculated with the seed culture. The media and protocols used were as follows.

The seed medium consisted of IX Bonner-Vogel salts (9.6 mM citric acid, 57 mM $K_2HPO_4$, 16.8 mM $NaNH_4HPO_4$, 0.8 mM $MgSO_4$), +25 mM $(NH_4)_2SO_4$, 2 mM $MgSO_4$, 10 μg/ml thiamine-HCl, 0.2% glucose, 0.25% casamino acids, and 100 μg/ml ampicillin and methicillin. The medium was formulated from sterile stock solutions, then filter-sterilized prior to use.

The fermentation medium consisted of 1X Bonner-Vogel salts (9.6 mM citric acid, 57 mM $K_2HPO_4$, 16.8 mM $NaNH_4HPO_4$, 0.8 mM $MgSO_4$), +25 mM $(NH_4)_2SO_4$, 2 mM $MgSO_4$, 10 μM $MnSO_4$, 6.9 μM $ZnCl_2$, 8.4 μM $CoCl_2$, 8.3 μM $NaMoO_4$, 6.8 μM $CaCl_2$, 7.4 μM $CuCl_2$, 8.1 μM $H_3BO_3$, 1 μM $FeCl_3$, 0.5 ml/l Macoll P2000 antifoam, 10 μg/ml thiamine HCl, 1.6% glucose, 2.0% casamino acids, and 100 μg/ml ampicillin. The above ingredients (through the antifoam) were sterilized in situ at 121° C. for 20 minutes, and the rest added from sterile, stock solutions, just prior to inoculation.

The seed culture was grown in a 100 ml flask of seed medium inoculated with 0.1 ml of frozen expression system cells. Following inoculation, the culture was shaken overnight at 30° C. The entire flask culture was used to inoculate a 10 liter fermentor culture.

Fermentation was carried out as follows. The initial temperature was 30° C., the pH was controlled at 6.9+/-0.1 with 4N $NH_4OH$ and glacial acetic acid, and the dissolved oxygen controlled at 30% by adjusting the agitation rate as needed from an initial, minimum value of 300 rpm. The aeration rate was held constant at 5 liters per minute. When the culture reached 2.5 OD (680 nm), after about 6–7.5 hours, the temperature was shifted to 38.5° C. to induce synthesis of the DNA polymerase using a ramp rate of 0.40° C./minute. The fermentation was allowed to continue overnight, to a total run time of about 24 hours. Cell paste was harvested by cross-flow filtration and centrifugation, and frozen at −20° C.

EXAMPLE 3

Purification of the Recombinant DNA Polymerase

This example describes the purification of the expressed F730YTma30 DNA Polymerase from the fermentation described above. The purification was carried out essentially as described in Lawyer et al., 1993, *PCR Method and Applications* 2:275–287, with modifications as described below.

The following standard abbreviations are used.
PEI=polyethylenimine
TLCK=N-α-p-tosyl-L-lysine chloromethyl ketone-HCl
PEI is available commercially from, among others, Polysciences, Inc. (Warrington, Pa.).
TLCK is available commercially from, among others, Sigma Chemical Co. (St. Louis, Mo.).

Approximately 150 grams of frozen (−70° C.) cells from the fermentation were thawed in lysis buffer (50 mM Tris-HCl, pH 7.5) containing 10 mM EDTA, 1 mM dithiothreitol (DTT), 2 mM Pefabloc SC (CenterChem, Inc., Stamford, Conn.); 1 μg/ml Leupeptin (Boehringer Mannheim, Indianapolis, Ind.), and 1 mM TLCK. The cells were lysed by passage five times through a Microfluidizer at 10,000 psi. The lysate was diluted with lysis buffer to a final volume of 5.5×cell wet weight. The resulting lysate was designated Fraction I.

Ammonium sulfate was gradually added to the Fraction I lysate to a concentration of 0.2 M. Fraction I then was PEI-precipitated as follows.

PEI titrations were used to determine the minimum amount of PEI necessary to precipitate nucleic acids. Ten μl of each trial precipitation were added to 100 μl of 0.5 μg/ml Ethidium Bromide in a standard microwell plate. Standards consisted of appropriately diluted lysate containing no PEI. The plate was illuminated with UV light, and the concentration of PEI needed to remove at least 99% of the nucleic acid was determined.

PEI was added slowly with stirring to 0.4% (concentration as determined from the titrations). The PEI treated lysate was centrifuged in a JA-10 rotor (500 ml bottles) at 8,000 RPM (11,300×g) for 30 minutes at 5° C. The supernatant (Fraction II) was decanted and retained.

Ammonium sulfate was added to the Fraction II supernatant to a concentration of 0.4 M. Fraction II then was heat-treated as follows.

The heat treatment was carried out in a 3 liter Braun fermentor. The agitation rate was 250 rpm. The temperature was increased to 75° C. over 6 minutes, held for 15 minutes, then cooled in the fermentor to 30° C. as rapidly as possible. The heat-treated Fraction II supernatant from the PEI precipitation was removed from the fermentor and held on ice for at least 30 minutes, then centrifuged as described above. The supernatant (Fraction III) was decanted and retained.

Fraction III was subjected to phenyl sepharose column chromatography as follows. A 250 ml radial flow column (Sepragen Corp., Hayward, Calif.) was packed with Phenyl Sepharose Fast Flow (High Sub) (Pharmacia, Piscataway, N.J.). Fraction III was diluted with 50 mM Tris (pH 7.5), 10 mM EDTA to reduce the ammonium sulfate to 0.3 M and then applied to the column. The column was washed (flow rate of 50 ml/minute) for 15–20 minutes (3–4 column volumes) in each of the following 4 buffers: (1) 50 mM Tris, pH 7.5, 10 mM EDTA, 0.3 M ammonium sulfate, 1 mM DTT; (2) 25 mM Tris, pH 7.5, 1 mM EDTA, 1 mM DTT; (3) 25 mM Tris, pH 7.5, 1 mM EDTA, 20% v/v ethylene glycol, 1 mM DTT; and (4) 25 mM Tris, pH 7.5, 1 mM EDTA, 20% v/v ethylene glycol, 1 mM DTT, 2.0 M urea. The urea eluate containing the DNA polymerase (Fraction IV) was collected as a single pool from approximately 3 to 18 minutes of the urea elution. The entire phenyl sepharose column step was completed in under 2 hours.

Fraction IV was subjected to heparin sepharose column chromatography as follows. Fraction IV (about 750 ml) was made 0.05 M in KCl (from a 3 M stock) and then loaded onto a 100 ml radial flow heparin sepharose column, which had been equilibrated in 25 mM Tris, pH 7.5, 1 mM EDTA, 0.05 M KCl, 1 mM DTT. After the load, the column was washed (flow rate of 20 ml/minute) for 30 minutes in equilibration buffer, then in 25 mM Tris, pH 7.5, 1 mM EDTA, 0.10 M KCl, 1 mM DTT. Finally the DNA polymerase was eluted in a 12 column volume gradient in 25 mM Tris, pH 7.5, 1 mM EDTA, and 0.10 to 0.5 M KCl, 1 mM DTT, collecting 75 fractions of 16 ml each. The heparin sepharose column step was completed in less than 3 hours. Fractions were analyzed by SDS-PAGE and some early fractions containing DNA polymerase that are less pure were removed from the pool (Fraction V).

Fraction V was concentrated to 20 ml on an Amicon YM30 membrane (Amicon Inc., Beverly, Mass.). The concentrate was dialyzed overnight at 4° C. against 3X storage buffer (60 mM Tris, pH 8.0, 0.3 mM EDTA, 0.3 mM KCl, 3 mM DTT). Glycerol was added to the dialysate to a final concentration of 50% (v/v) from an 80% (v/v) stock. Tween 20™ was added was added to a final concentration of 0.2% (w/v) from a 10% (w/v) stock. Sterile water was added to bring the volume of the preparation to 3 times the volume of the original lysate, yielding Fraction VI, a storage-stable preparation of F730YTma30 DNA Polymerase.

Fraction VI was assayed for DNA polymerase activity essentially as described in Lawyer et al., 1989, *J. Biol. Chem.* 264:6427, incorporated herein by reference.

EXAMPLE 4

Extension Rate

The extension rate of the F730YTma30 DNA Polymerase was measured using a template-limited primer extension assay. The assay was carried out using an excess of DNA polymerase, under which conditions the rate of extension is independent of the DNA polymerase concentration.

The chimeric enzyme of the present invention, F730YTma30 DNA Polymerase, was compared to F730YTma31 DNA Polymerase, expressed from plasmid pTMA31[F730Y], described above. F730YTma31 DNA Polymerase is a mutated version of UlTma™ DNA Polymerase (Perkin Elmer, Norwalk, Conn.) that incorporates the D323A and E325A mutations which inactivate the 3' to 5' exonuclease activity, and the F730Y mutation. F730YTma30 DNA Polymerase and F731YTma31 DNA Polymerase differ primarily in that F730YTma30 DNA Polymerase contains the 5'-nuclease domain from Taq DNA polymerase which has been mutated to inactivate the 5'-nuclease activity, whereas F730YTma31 DNA Polymerase is missing the first 283 amino acids of Tma DNA polymerase. Accordingly, F730YTma31 DNA Polymerase lacks 5'-nuclease activity as a result of a deletion of most of the 5'-nuclease domain.

DNA polymerase preparations first were assayed as described in Lawyer et al., 1989, *J. Biol. Chem.* 264:6427, to determine the unit concentration and to determine an amount of enzyme needed such that the enzyme would be in excess. Based on these assays, it was determined that the use of 1 unit of F730YTma30 DNA Polymerase or 3.5 units of F730YTma31 DNA Polymerase in the extension rate assay described below was sufficient to insure that the extension rate would be independent of enzyme concentration. The definition of a unit of enzyme is as defined in Lawyer et al., 1989, supra.

Extension rate was assayed for 3 minutes at 75° C. in a 50 µl reaction mixture containing 5 µl of DNA polymerase (diluted as described in Lawyer et al., 1989, supra, to contain the unit amount described above) and 45 µl of a reaction buffer containing 50 mM Bicine, pH 8.3, 25° C.; 2.5 mM MgCl$_2$; 1 mM β-mercaptoethanol; 200 µM each of dATP, dGTP and dTTP; 100 µM [α-$^{33}$P]dCTP (0.8 µCi/reaction); and 0.075 pmoles of the M13mp18 (Perkin Elmer, Norwalk, Conn.) template DNA preannealed to primer DG48, (SEQ ID NO: 11; 5'-GGGAAGGGCGATCGGTGCGGGCCTCTTCGC). The reactions were stopped by the addition of 10 µl 60 mM EDTA and stored at 0° C.

A 25 µl portion of the stopped reaction was diluted with 1 ml of 2 mM EDTA with 50 µg/ml sheared salmon sperm DNA as a carrier. The DNA was precipitated by the addition of 1 ml 20% trichloroacetic acid (w/v) and 2% sodium pyrophosphate, and incubated at 0° C. for 15 minutes. Precipitated DNA was collected on GF/C filter discs (Whatman International Ltd., Maidstone, England) and washed extensively with 5% trichloroacetic acid and 2% sodium pyrophosphate, then with 5% trichloroacetic acid, then with 5 ml of 95% ethanol, dried, and counted.

The amount of [α-$^{33}$P]dCMP incorporated per minute was determined for each sample. The data shown below represent the average of two reactions.

| DNA Polymerase | CPM |
| --- | --- |
| F730YTma30 | 1575 |
| F730YTma31 | 1116 |
| Ratio | 1.41 |

The data indicate that, as measured by the above assay, F730YTma30 DNA Polymerase has a 41% greater extension rate than F730YTma31 DNA Polymerase. In view of the difference between the two enzymes, the data indicate that the presence in F730YTma30 DNA Polymerase of the 5'-nuclease domain from Taq DNA polymerase, although inactivated by the G46D mutation, results in a significantly higher extension rate.

The extension products from a series of time points were analyzed further by denaturing agarose gel electrophoresis, which confirmed that the results represent an increase in the extension rate of the enzyme.

EXAMPLE 5

Dye Terminator Cycle Sequencing

This example demonstrates the application of the F730YTma30 DNA Polymerase to dye-labeled, dideoxy-terminator cycle sequencing. For comparison, cycle sequencing reactions also were carried out using AmpliTaq® DNA Polymerase, FS, a mutant form of Taq DNA polymerase that lacks exonuclease activity and incorporates an F667Y mutation, which is analogous to the F730Y mutation in F730YTma30 DNA Polymerase.

Cycle sequencing reactions were carried out using the reagents and protocols of the ABI PRISM™ Dye Terminator Cycle Sequencing Core Kit with AmpliTaq® DNA Polymerase, FS (Perkin Elmer, Norwalk, Conn.). The separate packaging of the reagents in this kit allowed for easy substitution of F730YTma DNA polymerase for AmpliTaq® DNA Polymerase, FS. In the kit, the AmpliTaq® DNA Polymerase, FS is provided combined with rTth Thermostable Inorganic Pyrophosphatase. For reactions using F730YTma30 DNA Polymerase, the DNA polymerase/pyrophosphatase mixture of the kit was replaced with 10 units of F730YTma30 DNA Polymerase and 20 units of rTth Thermostable Inorganic Pyrophosphatase. rTth Thermostable Inorganic Pyrophosphatase is described in copending U.S. patent application Ser. No. 08/528,384, incorporated herein by reference, now allowed.

The positive control template, pGEM®-3Zf(+) and primer, −21 M13, supplied with the kit were used. Reactions were carried out in a GeneAmp® PCR System 9600 thermal cycler (Perkin-Elmer, Norwalk, Conn.) using the recommended thermal cycling protocol (25 cycles: 96° C. for 10 seconds; 50° C. for 5 second; and 60° C. for 4 minutes).

Extension products were purified of unincorporated dye terminators by spin column purification using a Centri-Sep™ column from Princeton Separations (Adelphia, N.J.) and dried in a vacuum centrifuge, as recommended in the protocol. Samples were resuspended in 6 µl of loading buffer (deionized formamide and 25 mM EDTA (pH 8.0) containing 50 mg/l Blue dextran in a ratio of 5:1 formamide to EDTA/Blue dextran). The samples were votexed, spun, heated to 90° C. for 3 minutes to denature, and then directly loaded onto a pre-electrophoresed 48 cm (well-to-read) 4% polyacrylamide/6 M urea gel and electrophoresed and analyzed on an ABI PRISM™ 377 DNA Sequencer (Perkin Elmer, Norwalk, Conn.) according to the manufacturer's instructions.

Figure 2B:
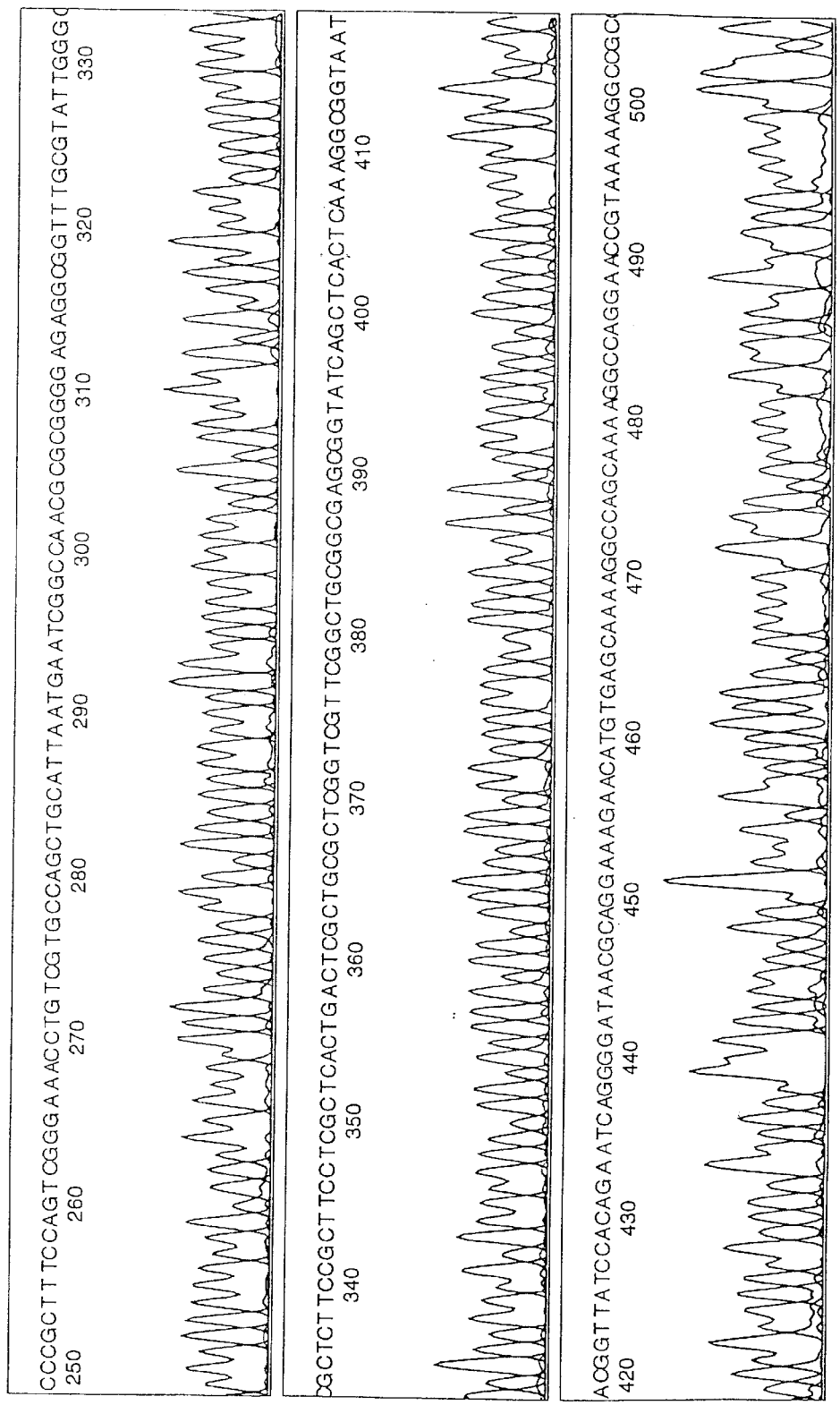
Figure 2C:
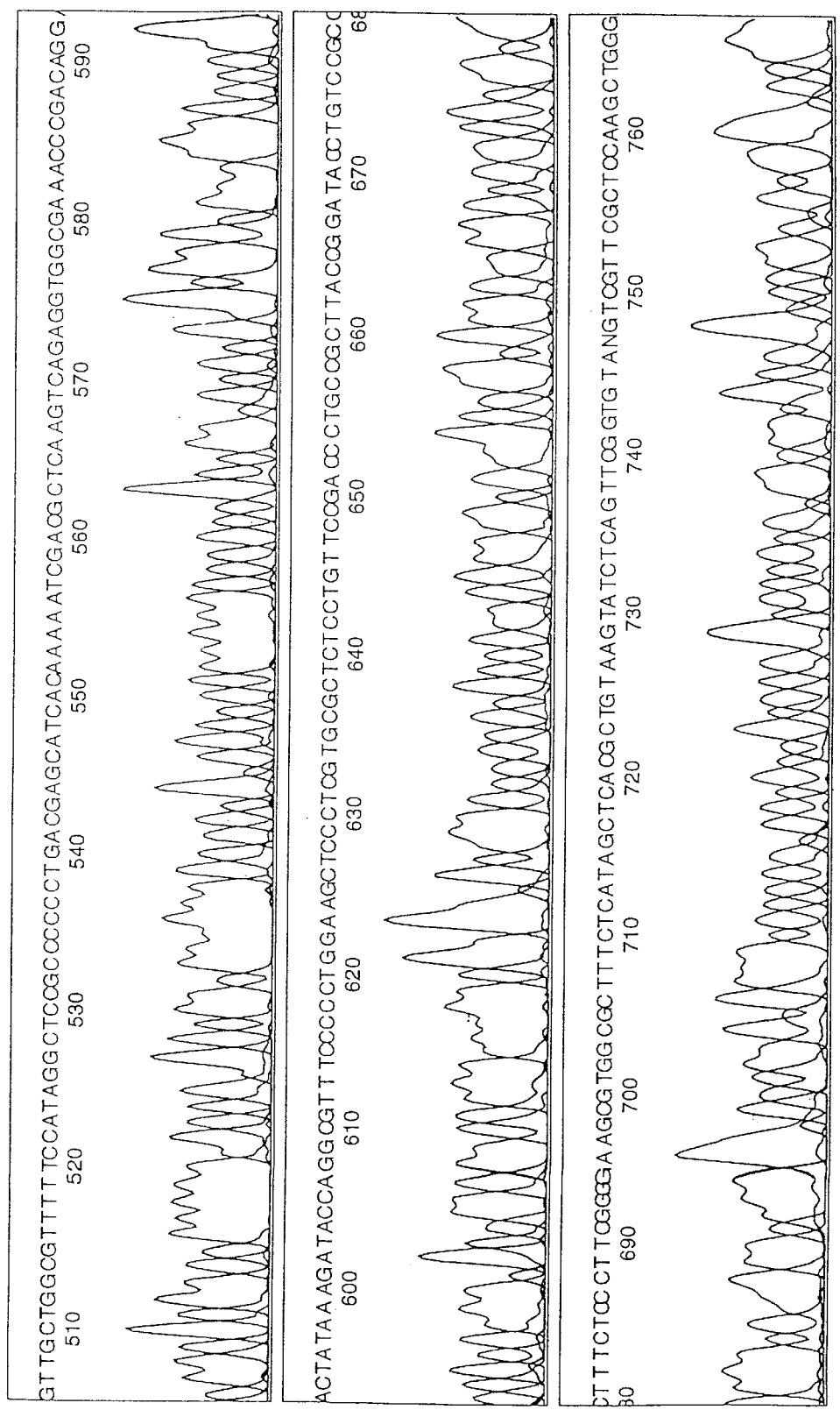
Figure 3A:
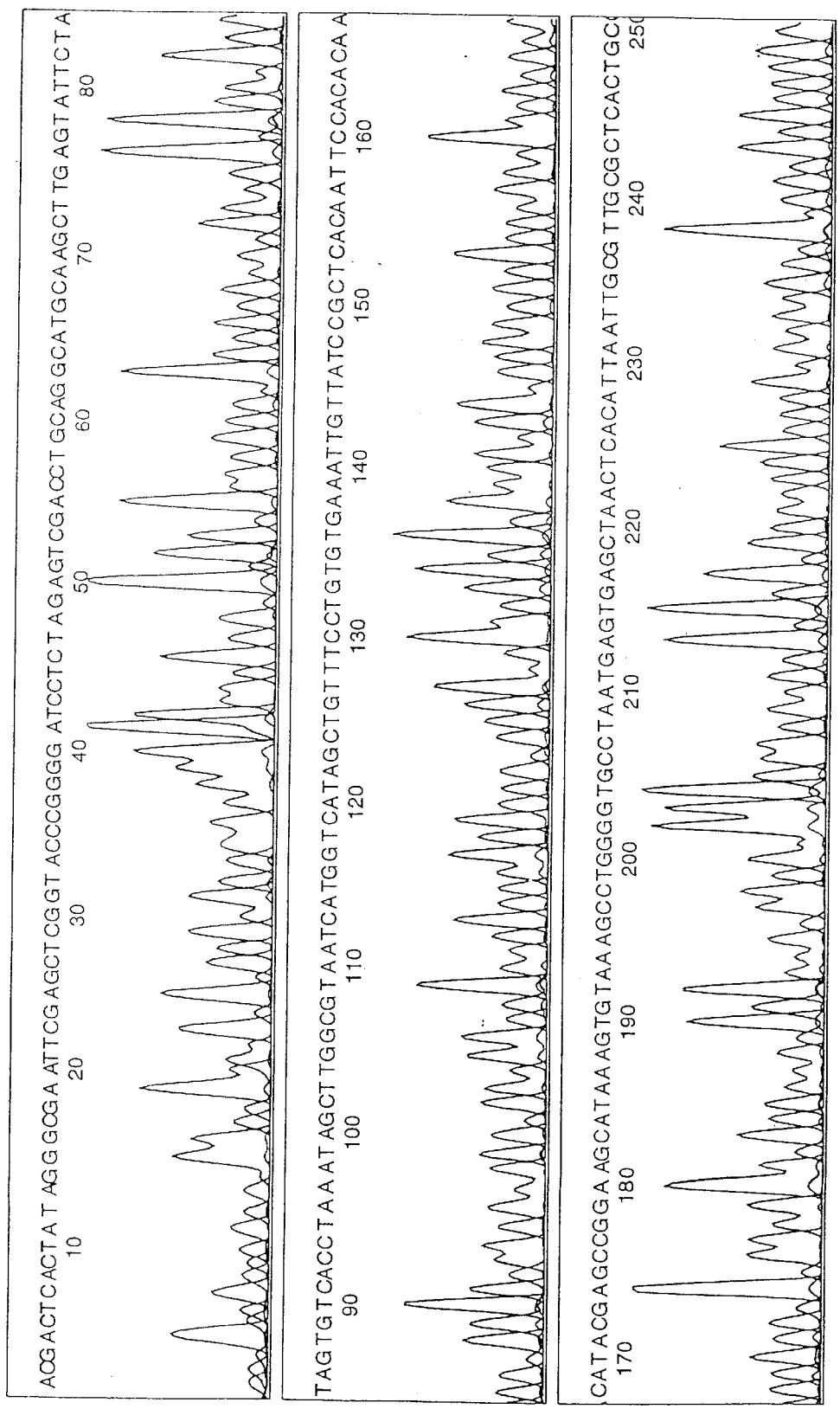
FIGS. 3A, 3B, and 3C provide a sequencing trace from the cycle sequencing reaction using AmpliTaq® DNA Polymerase, FS described in Example 5.
Figure 3B:
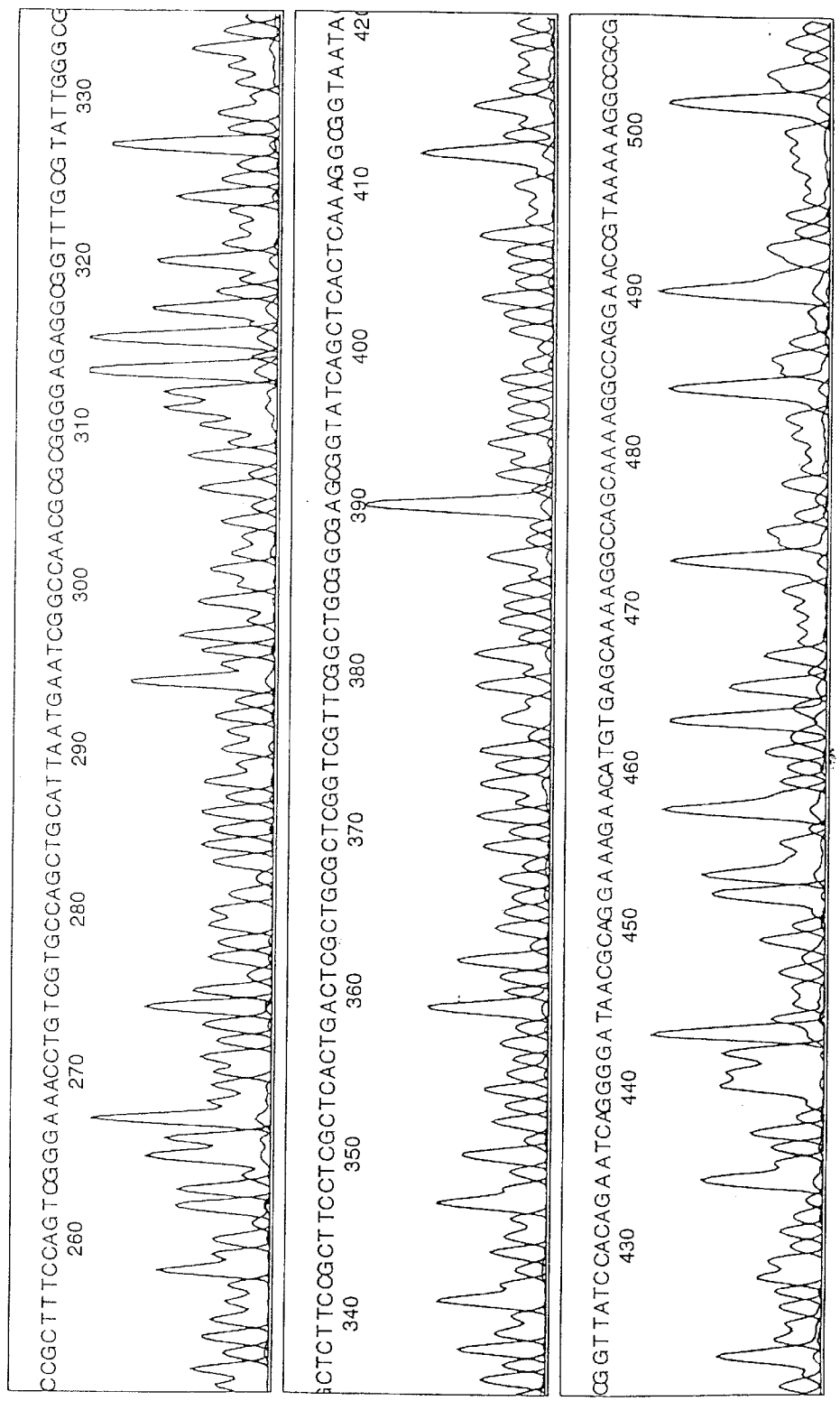
Figure 3C:
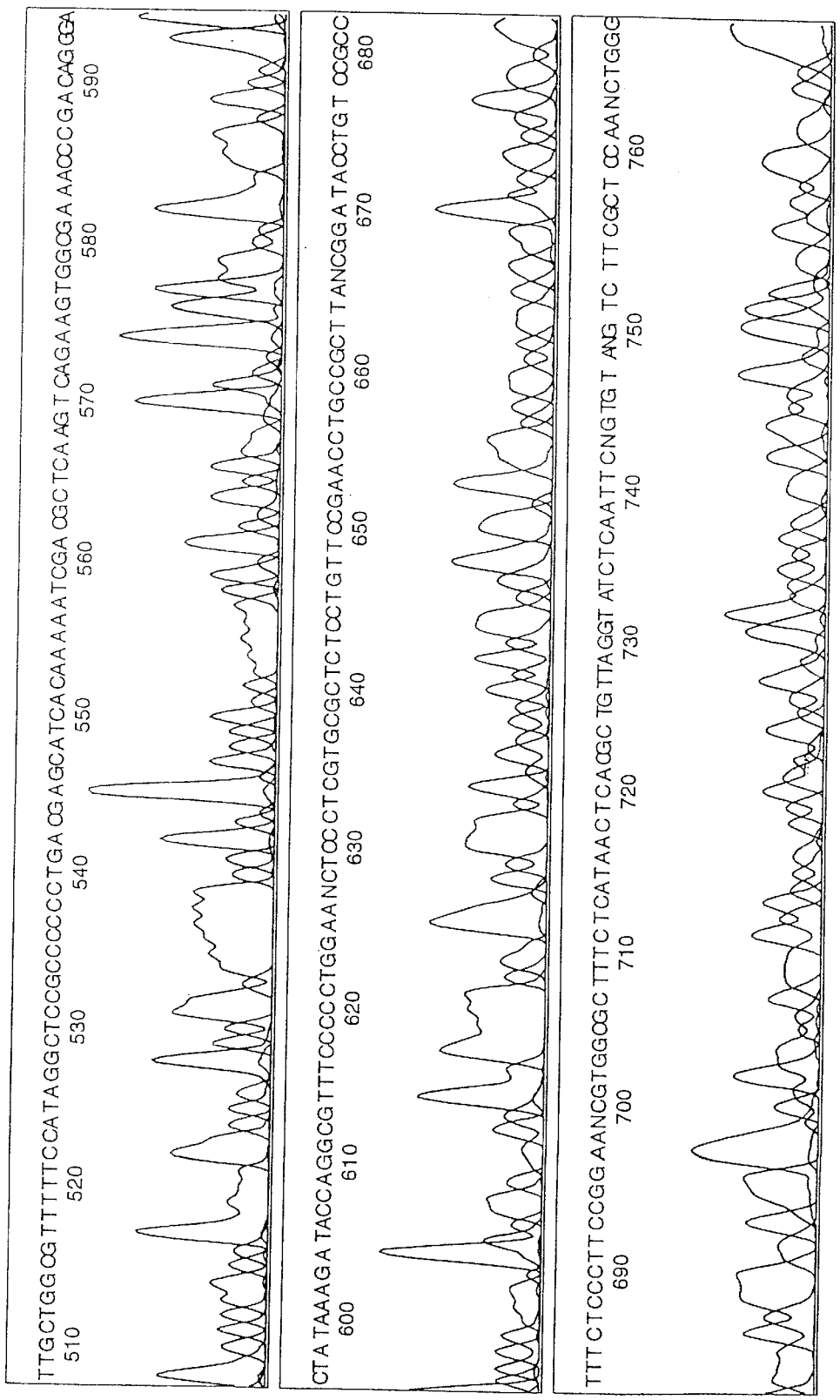

The resulting sequencing traces are shown in the figures. FIGS. 2A, 2B, and 2C provide a sequencing trace from a cycle sequencing reaction using F730YTma30 DNA Polymerase, and FIGS. 3A, 3B, and 3C provide sequencing trace from a cycle sequencing reaction using AmpliTaq® DNA Polymerase, FS. The base calling was set to begin with the tenth nucleotide from the primer.

It is clear from a comparison of the sequence tracings that the use of F730YTma30 DNA Polymerase results in a significant improvement in the overall uniformity of peak heights when compared to the results obtained using AmpliTaq® DNA Polymerase, FS. In particular, the use of F730YTma30 DNA Polymerase significantly increases the peak heights of those bases which, because of the DNA sequence context, result in very low peak heights when AmpliTaq® DNA Polymerase, FS is used, such as G after A or C, A after A or C, and T after T. Similarly, the use of F730YTma30 DNA Polymerase significantly decreases the peak height of those bases which, because of the DNA sequence context, result in very high peak heights when AmpliTaq® DNA Polymerase, FS is used, such as A after G. The uniformity of peak heights contributes to an increase in the accuracy of the sequencing.

The accuracy of the sequencing, i.e., the fraction of bases correctly sequenced, averaged for two duplicated reactions, was calculated from the results of the automated base-calling by the ABI PRISM™ 377 DNA Sequencing System analysis software. The results are summarized in the table, below. Typically, sequencing errors are most prevalent in the region next to the primer and the terminal regions away from the primer. Consequently, the first 10 nucleotides following the primer were ignored and the accuracy was calculated separately for the subsequent 50 nucleotides, the next 500 nucleotides, and finally two terminal regions, each 100 nucleotides in length.

Comparison of Sequencing Accuracy

| | nucleotide position: | | | |
|---|---|---|---|---|
| | 11–60 | 61–560 | 561–660 | 661–760 |
| F730YTma DNA Polymerase | 95% | 100% | 100% | 97.5% |
| AmpliTaq ® DNA Polymerase, FS | 97% | 99% | 97% | 88.5% |

The results demonstrate that F730YTma30 DNA Polymerase provides a substantial improvement in sequencing accuracy; strikingly so at longer read lengths (>560 nucleotides). The use of F730YTma30 DNA Polymerase completely eliminated errors in the 500 nucleotide region from nucleotides 51–550 and the first terminal region from nucleotides 551–650. Furthermore, the use of F730YTma30 DNA Polymerase extended the length of target sequencable with an accuracy of at least 97% by at least 100 nucleotides, from 650 nucleotides using AmpliTaq® DNA Polymerase, FS, to at least 750 nucleotides using F730YTma30 DNA Polymerase.

EXAMPLE 6

Dye Primer Cycle Sequencing

This example demonstrates the application of the DNA polymerase of the invention to dye primer sequencing.

Cycle sequencing reactions are performed in a buffer consisting of 25 mM Tris-HCl (pH 9.1) and 3.5 mM $MgCl_2$. Four individual reactions, one for each of the four dideoxy terminators, are performed. Reaction conditions for each of the four reactions are described below:

1. Dideoxy-ATP reactions (5 µl):
    100 µM each dATP, dCTP, and dTTP (Perkin-Elmer),
    100 µM c7dGTP (Pharmacia, Piscataway, N.J.),
    0.5 µM ddATP (Pharmacia),
    0.1 µg M13mp18 single-strand DNA template (Perkin-Elmer),
    0.4 pmol JOE Dye Primer (Perkin-Elmer),
    1 unit DNA polymerase, and
    5 units of rTth Thermostable Inorganic Pyrophosphatase.
2. Dideoxy-CTP reactions (5 µl):
    100 µM each dATP, dCTP, and dTTP (Perkin-Elmer),
    100 µM c7dGTP (Pharmacia),
    0.5 µM ddCTP (Pharmacia),
    0.1 µg M13mp18 single-strand DNA template (Perkin-Elmer),
    0.4 pmol FAM Dye Primer (Perkin-Elmer),
    1 unit DNA polymerase, and
    5 units of rTth Thermostable Inorganic Pyrophosphatase.
3. Dideoxy-GTP reactions (10 µl):
    100 µM each dATP, dCTP, and dTTP (Perkin-Elmer),
    100 µM c7dGTP (Pharmacia),
    0.5 µM ddGTP (Pharmacia),
    0.2 µg M13mp18 single-strand DNA template (Perkin-Elmer),
    0.8 pmol TAMRA Dye Primer (Perkin-Elmer),
    2 units DNA polymerase, and
    10 units of rTth Thermostable Inorganic Pyrophosphatase.

4. Dideoxy-TTP reactions (10 μl):

100 μM each dATP, dCTP, and dTTP (Perkin-Elmer),

100 μM c7dGTP (Pharmacia), 0.5 μM ddTTP (Pharmacia), 0.2 μg M13mp18 single-strand DNA template (Perkin-Elmer), 0.8 pmol ROX Dye Primer (Perkin-Elmer), 2 units DNA polymerase, and 10 units of rTth Thermostable Inorganic Pyrophosphatase.

Each of the four reactions are placed in a preheated (75° C.) Perkin-Elmer GeneAmp® PCR System 9600 thermal cycler and subjected to 15 cycles of 96° C. for 15 seconds, 55° C. for 1 second, and 70° C. for 1 minute, followed by 15 cycles of 96° C. for 15 seconds and 70° C. for 1 minute. The four reactions are pooled and precipitated by the addition of 100 μl 95% ethanol and 2.0 μl 3 M sodium acetate (pH 5.3) at 4° C. for 15 minutes. The pooled reaction is microcentrifuged for 15 minutes to collect precipitate, the supernatant is removed, and the pellet dried. The pellet is resuspended in 6 μl of deionized formamide/50 mM EDTA (pH 8.0) 5/1 (v/v), heated at 90° C. for 2 minutes, and directly loaded onto a pre-electrophoresed 4% polyacrylamide/6 M urea gel and electrophoresed and analyzed on an ABI PRISM™ 377 DNA Sequencer (Perkin Elmer, Norwalk, Conn.) according to the manufacturer instructions.

EXAMPLE 7

Effect of Pyrophosphatase

In the dye-terminator reactions described in Example 5, above, 20 units of rTth Thermostable Inorganic Pyrophosphatase (PPase) were added to the reaction to reduce the effects of pyrophosphorolysis. This amount of PPase had been determined to be beneficial for reactions using AmpliTaq® DNA Polymerase, FS. The following experiments were carried out to determine the effect of PPase concentration on the results of cycle sequencing reactions using F730YTma30 DNA Polymerase.

Dye-terminator cycle sequencing reactions were carried out essentially as described in Example 5, above, with the exception that the PPase concentration was varied between reactions. PPase concentrations of 0, 0.5, 1, and 20 units per reaction were tested. The target DNA, pGEM-3Zf(+), and the primer used, M13(-21), were from the ABI PRISM™ Dye Terminator Cycle Sequencing Core Kit, from Perkin Elmer (Norwalk, Conn.). All reactions were done in duplicate.

The results of each sequencing reaction were compared by direct comparison of the sequencing traces. The results revealed no obvious differences between the four PPase concentrations. Sequencing trace peak heights and background were comparable to a read of at least 500 base pairs. Thus, the data indicate that the use of F730YTma30 DNA Polymerase allows cycle sequencing reactions to be carried out without added Ppase.

EXAMPLE 8

Optimal dITP Concentration

The ABI PRISM™ Dye Terminator Cycle Sequencing Core Kit with AmpliTaq® DNA Polymerase, FS (Perkin Elmer, Norwalk, Conn.), used in Example 5, above, provides a dNTP mix containing dITP, dATP, dCTP, and dTTP in a 5:1:1:1 ratio. The increased concentration of dITP compensates for the lower dITP incorporation efficiency possessed by AmpliTaq® DNA Polymerase, FS. An analysis of the strength of the G signal peaks generated in the cycle sequencing reactions described in Example 5 suggested that F730YTma30 DNA Polymerase incorporates dITP with greater efficiency and, consequently, the dITP concentration should be decreased. Further reactions were carried out to determine an optimal concentration of dITP for use in dye-terminator cycle sequencing reactions using F730YTma30 DNA Polymerase.

Reactions were carried out essentially as described in Example 5, using the ABI PRISM™ Dye Terminator Cycle Sequencing Core Kit with AmpliTaq® DNA Polymerase, FS. In place of the dNTP mix provided with the kit, dNTP mixes containing 100 μM each dATP, dCTP, and dTTP, and a range of dITP concentrations in a TE buffer (10 mM Tris-HCl, pH 8, 0.1 mM EDTA) were used. As described in Example 5, a F730YTma30 DNA Polymerase/rTth Thermostable Inorganic Pyrophosphatase mixture was substituted for the AmpliTaq® DNA Polymerase, FS/rTth Thermostable Inorganic Pyrophosphatase mixture provided with the kit.

The optimal dITP concentration was determined by comparisons of both the sequence traces and the unprocessed signal strength data. Based on these experiments, it was determined that the dITP concentration is preferably lowered to 150–250 μM. The results indicate that F730YTma30 DNA Polymerase incorporates dITP significantly more efficiently than does AmpliTaq® DNA Polymerase, FS.

Further experiments carried out comparing F730YTma30 DNA Polymerase to other thermostable DNA polymerases (results not shown) also indicated that F730YTma30 DNA Polymerase possesses a significantly increased efficiency of dITP incorporation relative to other thermostable DNA polymerases.

Deposits

The following deposit was made on the date given:

| Strain | ATCC No. | Deposit Date |
| --- | --- | --- |
| pUC18:Tma25 | 98443 | May 28, 1997 |

This deposit was made under the provisions of the Budapest Treaty on the International Recognition of the Deposit of Microorganisms for the Purposes of Patent Procedure and the Regulations thereunder (Budapest Treaty). This assures maintenance of a viable culture for 30 years from date of deposit. The organism will be made available by ATCC under the terms of the Budapest Treaty, and subject to an agreement between Applicants and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638). The assignee of the present application agrees that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

We claim:

1. A thermostable DNA polymerase consisting of an N-terminal region and a C-terminal region, wherein said N-terminal region consists of amino acids 1 through n of a Thermus species DNA polymerase, wherein n is an amino acid corresponding to an amino acid m of a *Thermatoga maritima* (Tma) DNA polymerase described by SEQ ID NO: 10, wherein m is between 137 and 291;

wherein said C-terminal region consists of amino acids m+1 through 893 of said Tma DNA polymerase;

wherein said N-terminal region is modified by at least one point mutation, each characterized in that it substantially reduces or eliminates 5'-nuclease activity when present in said Thermus species DNA polymerase, or said C-terminal region is modified by at least one point mutation within the region that is amino acids m+1 to 291 of Tma DNA polymerase, each characterized in that it substantially reduces or eliminates 5'-nuclease activity when present in Tma DNA polymerase;

wherein said C-terminal region is modified by at least one point mutation, each characterized in that it substantially reduces 3' to 5' exonuclease activity when present in Tma DNA polymerase; and wherein said C-terminal region is modified to contain a tyrosine at amino acid 730.

2. A thermostable DNA polymerase of claim 1, wherein said N-terminal region contains a point mutation at an amino acid position corresponding to an amino acid in Taq DNA polymerase selected from the group consisting of D18, R25, G46, D67, F73, R74, Y81, G107, E117, D119, D120, D142, D144, G187, D188, D191, and G195.

3. A thermostable DNA polymerase of claim 1, wherein said C-terminal region contains a point mutation at an amino acid position selected from the group consisting of D323, E325, L329, N385, D389, L393, Y464, and D468.

4. A thermostable DNA polymerase of claim 2, wherein said N-terminal region contains an aspartic acid at an amino acid position corresponding to amino acid G46 in Taq DNA polymerase.

5. A thermostable DNA polymerase of claim 3, wherein said C-terminal region contains a D323A or E325A mutation.

6. A thermostable DNA polymerase of claim 1, wherein said Thermus species is selected from the group consisting of *Thermus aquaticus, Thermus flavus, Thermus thermophilus*, Thermus species Z05, *Thermus caldofilus*, Thermus species sps17, *Thermus filiformis*.

7. A thermostable DNA polymerase of claim 6, wherein said Thermus species is *Thermus aquaticus*.

8. A thermostable DNA polymerase of claim 7, wherein n=190.

9. A thermostable DNA polymerase of claim 8, wherein said N-terminal region contains an G46D mutation, and wherein said C-terminal region contains a D323A mutation and a E325A mutation.

10. An isolated DNA that encodes a thermostable DNA polymerase, wherein said thermostable DNA polymerase consists of an N-terminal region and a C-terminal region, wherein said N-terminal region consists of amino acids 1 through n of a Thermus species DNA polymerase, wherein n is an amino acid corresponding to an amino acid m of a *Thermatoga maritima* (Tma) DNA polymerase described by SEQ ID NO: 10, wherein m is between 137 and 291;

wherein said C-terminal region consists of amino acids m+1 through 893 of said Tma DNA polymerase;

wherein said N-terminal region is modified by at least one point mutation, each characterized in that it substantially reduces or eliminates 5'-nuclease activity when present in said Thermus species DNA polymerase, or said C-terminal region is modified by at least one point mutation within the region that is amino acids m+1 to 291 of Tma DNA polymerase, each characterized in that it substantially reduces or eliminates 5'-nuclease activity when present in Tma DNA polymerase;

wherein said C-terminal region is modified by at least one point mutation, each characterized in that it substantially reduces 3' to 5' exonuclease activity when present in Tma DNA polymerase; and wherein said C-terminal region is modified to contain a tyrosine at amino acid 730.

11. An isolated DNA of claim 10, wherein said N-terminal region contains a point mutation at an amino acid position corresponding to an amino acid in Taq DNA polymerase selected from the group consisting of D18, R25, G46, D67, F73, R74, Y81, G107, E117, D119, D120, D142, D144, G187, D188, D191, and G195.

12. An isolated DNA of claim 10, wherein said C-terminal region contains a point mutation at an amino acid position selected from the group consisting of D323, E325, L329, N385, D389, L393, Y464, and D468.

13. An isolated DNA of claim 11, wherein said N-terminal region contains an aspartic acid at an amino acid position corresponding to amino acid G46 in Taq DNA polymerase.

14. An isolated DNA of claim 12, wherein said C-terminal region contains a D323A or E325A mutation.

15. An isolated DNA of claim 10, wherein said Thermus species is selected from the group consisting of *Thermus aquaticus, Thermus flavus, Thermus thermophilis*, Thermus species Z05, *Thermus caldofilus*, Thermus species sps17, *Thermus filiformis*.

16. An isolated DNA of claim 15, wherein said Thermus species is *Thermus aquaticus*.

17. An isolated DNA of claim 16, wherein n=190.

18. An isolated DNA of claim 17, wherein said N-terminal region contains a G46D mutation, and wherein said C-terminal region contains a D323A mutation and a E325A mutation.

19. A plasmid comprising the isolated DNA of claim 10.
20. A plasmid comprising the isolated DNA of claim 11.
21. A plasmid comprising the isolated DNA of claim 12.
22. A plasmid comprising the isolated DNA of claim 13.
23. A plasmid comprising the isolated DNA of claim 14.
24. A plasmid comprising the isolated DNA of claim 15.
25. A plasmid comprising the isolated DNA of claim 16.
26. A plasmid comprising the isolated DNA of claim 17.
27. A plasmid comprising the isolated DNA of claim 18.
28. An expression vector comprising the isolated DNA of claim 19.
29. An expression vector comprising the isolated DNA of claim 20.
30. An expression vector comprising the isolated DNA of claim 21.
31. An expression vector comprising the isolated DNA of claim 22.
32. An expression vector comprising the isolated DNA of claim 23.
33. An expression vector comprising the isolated DNA of claim 24.
34. An expression vector comprising the isolated DNA of claim 25.
35. An expression vector comprising the isolated DNA of claim 26.
36. An expression vector comprising the isolated DNA of claim 27.
37. A host cell transformed with an expression vector of claim 28.
38. A host cell transformed with an expression vector of claim 29.
39. A host cell transformed with an expression vector of claim 30.
40. A host cell transformed with an expression vector of claim 31.
41. A host cell transformed with an expression vector of claim 32.
42. A host cell transformed with an expression vector of claim 33.
43. A host cell transformed with an expression vector of claim 34.
44. A host cell transformed with an expression vector of claim 35.

45. A host cell transformed with an expression vector of claim 36.

46. A method for preparing a thermostable DNA polymerase, comprising:
(a) culturing a host cell of claim 37 under conditions which promote the expression of thermostable DNA polymerase; and
(b) isolating thermostable DNA polymerase from said host cell.

47. A method for preparing a thermostable DNA polymerase, comprising:
(a) culturing a host cell of claim 38 under conditions which promote the expression of thermostable DNA polymerase; and
(b) isolating thermostable DNA polymerase from said host cell.

48. A method for preparing a thermostable DNA polymerase, comprising:
(a) culturing a host cell of claim 39 under conditions which promote the expression of thermostable DNA polymerase; and
(b) isolating thermostable DNA polymerase from said host cell.

49. A method for preparing a thermostable DNA polymerase, comprising:
(a) culturing a host cell of claim 40 under conditions which promote the expression of thermostable DNA polymerase; and
(b) isolating thermostable DNA polymerase from said host cell.

50. A method for preparing a thermostable DNA polymerase, comprising:
(a) culturing a host cell of claim 41 under conditions which promote the expression of thermostable DNA polymerase; and
(b) isolating thermostable DNA polymerase from said host cell.

51. A method for preparing a thermostable DNA polymerase, comprising:
(a) culturing a host cell of claim 42 under conditions which promote the expression of thermostable DNA polymerase; and
(b) isolating thermostable DNA polymerase from said host cell.

52. A method for preparing a thermostable DNA polymerase, comprising:
(a) culturing a host cell of claim 43 under conditions which promote the expression of thermostable DNA polymerase; and
(b) isolating thermostable DNA polymerase from said host cell.

53. A method for preparing a thermostable DNA polymerase, comprising:
(a) culturing a host cell of claim 44 under conditions which promote the expression of thermostable DNA polymerase; and
(b) isolating thermostable DNA polymerase from said host cell.

54. A method for preparing a thermostable DNA polymerase, comprising:
(a) culturing a host cell of claim 45 under conditions which promote the expression of thermostable DNA polymerase; and
(b) isolating thermostable DNA polymerase from said host cell.

55. A kit for carrying out a primer extension reaction, comprising a thermostable DNA Polymerase of claim 1.

56. A kit for carrying out a primer extension reaction, comprising a thermostable DNA Polymerase of claim 2.

57. A kit for carrying out a primer extension reaction, comprising a thermostable DNA Polymerase of claim 3.

58. A kit for carrying out a primer extension reaction, comprising a thermostable DNA Polymerase of claim 4.

59. A kit for carrying out a primer extension reaction, comprising a thermostable DNA Polymerase of claim 5.

60. A kit for carrying out a primer extension reaction, comprising a thermostable DNA Polymerase of claim 6.

61. A kit for carrying out a primer extension reaction, comprising a thermostable DNA Polymerase of claim 7.

62. A kit for carrying out a primer extension reaction, comprising a thermostable DNA Polymerase of claim 8.

63. A kit for carrying out a primer extension reaction, comprising a thermostable DNA Polymerase of claim 9.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Thr Tyr Gly Val Ala Arg Met Leu Val Arg Phe Ile Lys Asp
            35                  40                  45

His Ile Ile Val Gly Lys Asp Tyr Val Ala Val Ala Phe Asp Lys Lys
        50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
            115                 120                 125

Asp Glu Ile Phe Ile Val Thr Gly Asp Lys Asp Met Leu Gln Leu Val
            130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
            195                 200                 205

Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
            260                 265                 270

Pro Leu Leu Lys Glu Leu Glu Phe Ala Ser Ile Met Lys Glu Leu Gln
        275                 280                 285

Leu Tyr Glu
    290
```

(2) INFORMATION FOR SEQ ID NO:2:

(i) SEQUENCE CHARACTERISTICS:
    (A) LENGTH: 289 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                    85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                    165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                    245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu
```

(2) INFORMATION FOR SEQ ID NO:3:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Ala Met Leu Pro Leu Phe Glu Pro Lys Gly Arg Val Leu Leu Val
1               5                   10                  15

Asp Gly His His Leu Ala Tyr Arg Thr Phe Ala Leu Lys Gly Leu
            20                  25                  30

Thr Thr Ser Arg Gly Glu Pro Val Gln Ala Val Tyr Gly Phe Ala Lys
                35                  40                  45

Ser Leu Leu Lys Ala Leu Lys Glu Asp Gly Asp Val Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Ile Lys Glu Leu Val Asp Leu Leu Gly Leu Val Arg Leu Glu Val
                100                 105                 110

Pro Gly Phe Glu Ala Asp Asp Val Leu Ala Thr Leu Ala Lys Arg Ala
                115                 120                 125

Glu Lys Glu Gly Tyr Glu Val Arg Ile Leu Thr Ala Asp Arg Asp Leu
        130                 135                 140

Tyr Gln Leu Leu Ser Glu Arg Ile Ala Ile Leu His Pro Glu Gly Tyr
145                 150                 155                 160

Leu Ile Thr Pro Ala Trp Leu Tyr Glu Lys Tyr Gly Leu Arg Pro Glu
                165                 170                 175

Gln Trp Val Asp Tyr Arg Ala Leu Ala Gly Asp Pro Ser Asp Asn Ile
                180                 185                 190

Pro Gly Val Lys Gly Ile Gly Glu Lys Thr Ala Gln Arg Leu Ile Arg
                195                 200                 205

Glu Trp Gly Ser Leu Glu Asn Leu Phe Gln His Leu Asp Gln Val Lys
210                 215                 220

Pro Ser Leu Arg Glu Lys Leu Gln Ala Gly Met Glu Ala Leu Ala Leu
225                 230                 235                 240

Ser Arg Lys Leu Ser Gln Val His Thr Asp Leu Pro Leu Glu Val Asp
                245                 250                 255

Phe Gly Arg Arg Arg Thr Pro Asn Leu Glu Gly Leu Arg Ala Phe Leu
                260                 265                 270

Glu Arg Leu Glu Phe Gly Ser Leu Leu His Glu Phe Gly Leu Leu Glu
        275                 280                 285

(2) INFORMATION FOR SEQ ID NO:4:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Tyr Lys Ala Val Phe
    50                  55                  60
```

-continued

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu
    290

(2) INFORMATION FOR SEQ ID NO:5:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

```
Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu
    290

(2) INFORMATION FOR SEQ ID NO:6:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
            115                 120                 125

Asn Pro Glu Lys Glu Gly Tyr Glu Val Arg Ile Leu Thr Ala Asp Arg
        130                 135                 140

Asp Leu Asp Gln Leu Val Ser Asp Arg Val Ala Val Leu His Pro Glu
145                 150                 155                 160
```

```
Gly His Leu Ile Thr Pro Glu Trp Leu Trp Gln Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu
    290

(2) INFORMATION FOR SEQ ID NO:7:

(i) SEQUENCE CHARACTERISTICS:
        (A) LENGTH: 287 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Met Leu Pro Leu Phe Glu Pro Lys Gly Arg Val Leu Leu Val Asp Gly
1               5                   10                  15

His His Leu Ala Tyr Arg Thr Phe Phe Ala Leu Lys Gly Leu Thr Thr
                20                  25                  30

Ser Arg Gly Glu Pro Val Gln Ala Val Tyr Gly Phe Ala Lys Ser Leu
            35                  40                  45

Leu Lys Ala Leu Lys Glu Asp Gly Glu Val Ala Ile Val Val Phe Asp
    50                  55                  60

Ala Lys Ala Pro Ser Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
                100                 105                 110

Phe Glu Ala Asp Asp Val Leu Ala Thr Leu Ala Lys Lys Ala Glu Arg
            115                 120                 125

Glu Gly Tyr Glu Val Arg Ile Leu Ser Ala Asp Arg Asp Leu Tyr Gln
    130                 135                 140

Leu Leu Ser Asp Arg Ile His Leu Leu His Pro Glu Gly Glu Val Leu
145                 150                 155                 160

Thr Pro Gly Trp Leu Gln Glu Arg Tyr Gly Leu Ser Pro Glu Arg Trp
                165                 170                 175

Val Glu Tyr Arg Ala Leu Val Gly Asp Pro Ser Asp Asn Leu Pro Gly
            180                 185                 190

Val Pro Gly Ile Gly Glu Lys Thr Ala Leu Lys Leu Leu Lys Glu Trp
        195                 200                 205
```

```
Gly Ser Leu Glu Ala Ile Leu Lys Asn Leu Asp Gln Val Lys Pro Glu
    210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Ala Lys Arg Arg Glu Pro Asp Trp Glu Gly Leu Lys Ala Phe Leu Glu
                260                 265                 270

Arg Leu Glu Phe Gly Ser Leu Leu His Glu Phe Gly Leu Leu Glu
                275                 280                 285
```

(2) INFORMATION FOR SEQ ID NO:8:

(i) SEQUENCE CHARACTERISTICS:
       (A) LENGTH: 287 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:8:

```
Met Leu Pro Leu Leu Glu Pro Lys Gly Arg Val Leu Val Asp Gly
1               5                   10                  15

His His Leu Ala Tyr Arg Thr Phe Phe Ala Leu Lys Gly Leu Thr Thr
                20                  25                  30

Ser Arg Gly Glu Pro Val Gln Ala Val Tyr Gly Phe Ala Lys Ser Leu
            35                  40                  45

Leu Lys Ala Leu Lys Glu Asp Gly Glu Val Ala Ile Val Val Phe Asp
    50                  55                  60

Ala Lys Ala Pro Ser Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
                100                 105                 110

Phe Glu Ala Asp Asp Val Leu Ala Thr Leu Ala Arg Lys Ala Glu Arg
            115                 120                 125

Glu Gly Tyr Glu Val Arg Ile Leu Ser Ala Asp Arg Asp Leu Tyr Gln
    130                 135                 140

Leu Leu Ser Asp Arg Ile His Leu His Pro Glu Gly Glu Val Leu
145                 150                 155                 160

Thr Pro Gly Trp Leu Gln Glu Arg Tyr Gly Leu Ser Pro Glu Arg Trp
                165                 170                 175

Val Glu Tyr Arg Ala Leu Val Gly Asp Pro Ser Asp Asn Leu Pro Gly
            180                 185                 190

Val Pro Gly Ile Gly Glu Lys Thr Ala Leu Lys Leu Leu Lys Glu Trp
    195                 200                 205

Gly Ser Leu Glu Ala Ile Leu Lys Asn Leu Asp Gln Val Lys Pro Glu
    210                 215                 220

Arg Val Trp Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Ala Lys Arg Arg Glu Pro Asp Trp Glu Gly Leu Lys Ala Phe Leu Glu
                260                 265                 270
```

```
         Arg Leu Glu Phe Gly Ser Leu Leu His Glu Phe Gly Leu Leu Glu
             275                 280                 285

(2) INFORMATION FOR SEQ ID NO:9:

(i) SEQUENCE CHARACTERISTICS:
        (A) LENGTH: 2682 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATGAGAGGCA TGCTTCCACT TTTTGAGCCC AAGGGCCGGG TCCTCCTGGT GGACGGCCAC     60

CACCTGGCCT ACCGCACCTT CCACGCCCTG AAGGGCCTCA CCACCAGCCG GGGGGAGCCG    120

GTGCAGGCGG TCTACGACTT CGCCAAGAGC CTCCTCAAGG CCCTCAAGGA GGACGGGGAC    180

GCGGTGATCG TGGTCTTTGA CGCCAAGGCC CCCTCCTTCC GCCACGAGGC CTACGGTGGG    240

TACAAGGCGG GCCGGGCCCC CACGCCGGAG GACTTTCCCC GGCAACTCGC CCTCATCAAG    300

GAGCTGGTAG ATCTCCTGGG GCTGGCGCGC CTCGAGGTCC CGGGCTACGA GGCGGACGAC    360

GTCCTGGCCA GCCTGGCCAA GAAGGCGGAA AAGGAGGGCT ACGAGGTCCG CATCCTCACC    420

GCCGACAAAG ACCTTTACCA GCTCCTTTCC GACCGCATCC ACGTCCTCCA CCCCGAGGGG    480

TACCTCATCA CCCCGGCCTG GCTTTGGGAA AAGTACGGCC TGAGGCCCGA CCAGTGGGCC    540

GACTACCGGG CCCTGACCGG GGACGAGTCC GACAACATCC CCGGGGTCAC TGGGATCGGT    600

GAGAAGACTG CTGTTCAGCT TCTAGAGAAG TACAAAGACC TCGAAGACAT ACTGAATCAT    660

GTTCGCGAAC TTCCTCAAAA GGTGAGAAAA GCCCTGCTTC GAGACAGAGA AAACGCCATT    720

CTCAGCAAAA AGCTGGCGAT TCTGGAAACA AACGTTCCCA TTGAAATAAA CTGGGAAGAA    780

CTTCGCTACC AGGGCTACGA CAGAGAGAAA CTCTTACCAC TTTTGAAAGA ACTGGAATTC    840

GCATCCATCA TGAAGGAACT TCAACTGTAC GAAGAGTCCG AACCCGTTGG ATACAGAATA    900

GTGAAAGACC TAGTGGAATT TGAAAAACTC ATAGAGAAAC TGAGAGAATC CCCTTCGTTC    960

GCCATAGATC TTGAGACGTC TTCCCTCGAT CCTTTCGACT GCGACATTGT CGGTATCTCT   1020

GTGTCTTTCA AACCAAAGGA AGCGTACTAC ATACCACTCC ATCATAGAAA CGCCCAGAAC   1080

CTGGACGAAA AAGAGGTTCT GAAAAAGCTC AAAGAAATTC TGGAGGACCC CGGAGCAAAG   1140

ATCGTTGGTC AGAATTTGAA ATTCGATTAC AAGGTGTTGA TGGTGAAGGG TGTTGAACCT   1200

GTTCCTCCTT ACTTCGACAC GATGATAGCG GCTTACCTTC TTGAGCCGAA CGAAAAGAAG   1260

TTCAATCTGG ACGATCTCGC ATTGAAATTT CTTGGATACA AAATGACATC TTACCAAGAG   1320

CTCATGTCCT TCTCTTTTCC GCTGTTTGGT TTCAGTTTTG CCGATGTTCC TGTAGAAAAA   1380

GCAGCGAACT ACTCCTGTGA AGATGCAGAC ATCACCTACA GACTTTACAA GACCCTGAGC   1440

TTAAAACTCC ACGAGGCAGA TCTGGAAAAC GTGTTCTACA AGATAGAAAT GCCCCTTGTG   1500

AACGTGCTTG CACGGATGGA ACTGAACGGT GTGTATGTGG ACACAGAGTT CCTGAAGAAA   1560

CTCTCAGAAG AGTACGGAAA AAAACTCGAA GAACTGGCAG AGGAAATATA CAGGATAGCT   1620

GGAGAGCCGT TCAACATAAA CTCACCGAAG CAGGTTTCAA GGATCCTTTT TGAAAAACTC   1680

GGCATAAAAC CACGTGGTAA AACGACGAAA ACGGGAGACT ATTCAACACG CATAGAAGTC   1740

CTCGAGGAAC TTGCCGGTGA ACACGAAATC ATTCCTCTGA TTCTTGAATA CAGAAAGATA   1800

CAGAAATTGA AATCAACCTA CATAGACGCT CTTCCCAAGA TGGTCAACCC AAAGACCGGA   1860
```

```
AGGATTCATG CTTCTTTCAA TCAAACGGGG ACTGCCACTG GAAGACTTAG CAGCAGCGAT     1920

CCCAATCTTC AGAACCTCCC GACGAAAAGT GAAGAGGGAA AAGAAATCAG GAAAGCGATA     1980

GTTCCTCAGG ATCCAAACTG GTGGATCGTC AGTGCCGACT ACTCCCAAAT GAACTGAGG      2040

ATCCTCGCCC ATCTCAGTGG TGATGAGAAT CTTTTGAGGG CATTCGAAGA GGGCATCGAC     2100

GTCCACACTC TAACAGCTTC CAGAATATTC AACGTGAAAC CCGAAGAAGT AACCGAAGAA     2160

ATGCGCCGCG CTGGTAAAAT GGTTAATTTT TCCATCATAT ACGGTGTAAC ACCTTACGGT     2220

CTGTCTGTGA GGCTTGGAGT ACCTGTGAAA GAAGCAGAAA AGATGATCGT CAACTACTTC     2280

GTCCTCTACC CAAAGGTGCG CGATTACATT CAGAGGGTCG TATCGGAAGC GAAAGAAAAA     2340

GGCTATGTTA GAACGCTGTT TGGAAGAAAA AGAGACATAC CACAGCTCAT GGCCCGGGAC     2400

AGGAACACAC AGGCTGAAGG AGAACGAATT GCCATAAACA CTCCCATACA GGGTACAGCA     2460

GCGGATATAA TAAAGCTGGC TATGATAGAA ATAGACAGGG AACTGAAAGA AAGAAAAATG     2520

AGATCGAAGA TGATCATACA GGTCCACGAC GAACTGGTTT TTGAAGTGCC CAATGAGGAA     2580

AAGGACGCGC TCGTCGAGCT GGTGAAAGAC AGAATGACGA ATGTGGTAAA GCTTTCAGTG     2640

CCGCTCGAAG TGGATGTAAC CATCGGCAAA ACATGGTCGT GA                        2682

(2) INFORMATION FOR SEQ ID NO:10:

(i) SEQUENCE CHARACTERISTICS:
        (A) LENGTH: 893 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Thr Gly Ile Pro Thr
            20                  25                  30

Asn Ala Thr Tyr Gly Val Ala Arg Met Leu Val Arg Phe Ile Lys Asp
            35                  40                  45

His Ile Ile Val Gly Lys Asp Tyr Val Ala Val Ala Phe Asp Lys Lys
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
        115                 120                 125

Asp Glu Ile Phe Ile Val Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205
```

```
Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
            260                 265                 270

Pro Leu Leu Lys Glu Leu Glu Phe Ala Ser Ile Met Lys Glu Leu Gln
        275                 280                 285

Leu Tyr Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
    610                 615                 620
```

```
Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
            645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Gly Ile Asp Val His Thr Leu
        690             695             700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
            725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
            805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGGAAGGGCG ATCGGTGCGG GCCTCTTCGC          30